(12) United States Patent
Kojima et al.

(10) Patent No.: US 10,317,371 B2
(45) Date of Patent: Jun. 11, 2019

(54) ULTRASONIC TRANSDUCER, ULTRASONIC PROBE, ULTRASONIC APPARATUS, ULTRASONIC TRANSDUCER MANUFACTURING METHOD, AND VIBRATION DEVICE

(71) Applicant: Seiko Epson Corporation, Tokyo (JP)

(72) Inventors: Chikara Kojima, Matsumoto (JP); Koji Ohashi, Matsumoto (JP)

(73) Assignee: Seiko Epson Corporation (JP)

( * ) Notice: Subject to any disclaimer, the term of this patent is extended or adjusted under 35 U.S.C. 154(b) by 100 days.

(21) Appl. No.: 15/420,217

(22) Filed: Jan. 31, 2017

(65) Prior Publication Data

US 2017/0227502 A1  Aug. 10, 2017

(30) Foreign Application Priority Data

Feb. 4, 2016 (JP) ................. 2016-020036

(51) Int. Cl.
  *A61B 8/00* (2006.01)
  *G01N 29/24* (2006.01)

(52) U.S. Cl.
  CPC ............... *G01N 29/24* (2013.01); *A61B 8/00* (2013.01); *G01N 29/2437* (2013.01); *G01N 2291/101* (2013.01); *H04R 2400/00* (2013.01); *H04R 2410/00* (2013.01); *H04R 2499/11* (2013.01)

(58) Field of Classification Search
  CPC ............... G01N 29/24; G01N 29/2437; G01N 2291/101; A61B 8/00; H04R 2499/11; H04R 2410/00; H04R 2400/00
  See application file for complete search history.

(56) References Cited

U.S. PATENT DOCUMENTS

| | | | |
|---|---|---|---|
| 2014/0086017 A1* | 3/2014 | Nakano | G01F 1/662 367/180 |
| 2014/0211587 A1* | 7/2014 | Kiyose | G01S 15/8925 367/7 |
| 2015/0258573 A1 | 9/2015 | Kojima | |
| 2016/0066885 A1* | 3/2016 | Jin | A61B 8/4444 600/459 |

FOREIGN PATENT DOCUMENTS

| | | |
|---|---|---|
| JP | 2000-023289 A | 1/2000 |
| JP | 2000-121739 A | 4/2000 |
| JP | 2010-164331 A | 7/2010 |
| JP | 2015-188208 A | 10/2015 |

* cited by examiner

*Primary Examiner* — Justin Seo
*Assistant Examiner* — John M Royston
(74) *Attorney, Agent, or Firm* — Harness, Dickey & Pierce, P.L.C.

(57) ABSTRACT

An ultrasonic sensor includes: a substrate in which an opening is formed; a vibration film that is provided on the substrate so as to close the opening; a plurality of vibration elements that are disposed at positions where the vibration film and the opening overlap each other in a plan view along a thickness direction of the vibration film; a sealing plate that is disposed so as to face the vibration film, supports the vibration film, and has a surface facing the vibration film as a flat surface; and a suppressing portion that is provided between the adjacent vibration elements in the plan view, is bonded to both the vibration film and the sealing plate, and is formed of a resin material for suppressing transmission of vibration of the vibration film.

8 Claims, 11 Drawing Sheets

ULTRASONIC TRANSDUCER, ULTRASONIC PROBE, ULTRASONIC APPARATUS, ULTRASONIC TRANSDUCER MANUFACTURING METHOD, AND VIBRATION DEVICE

BACKGROUND

1. Technical Field

The present invention relates to an ultrasonic transducer, an ultrasonic probe, an ultrasonic apparatus, an ultrasonic transducer manufacturing method, a vibration device, and the like.

2. Related Art

An ultrasonic transducer including a base portion having an opening and a piezoelectric element, which is provided on a vibration film that closes the opening, is known. In such an ultrasonic transducer, it is possible to transmit ultrasonic waves by driving the piezoelectric element to vibrate the vibration film or to detect (receive) the vibration of the vibration film when ultrasonic waves are input to the vibration film using the piezoelectric element (for example, refer to JP-A-2010-164331).

The efficiency of transmission or reception of ultrasonic waves in such an ultrasonic transducer depends on the distortion in the film thickness direction of a region (vibration region) of the vibration film that closes the opening. In order to improve the efficiency of transmission or reception of ultrasonic waves, it is necessary to increase the distortion of the vibration region. In this case, the two-dimensional shape of the vibration region when the ultrasonic transducer is viewed from the film thickness direction may be set to have a low aspect ratio.

Incidentally, in an ultrasonic transducer such as that disclosed in JP-A-2010-164331, the frequency of ultrasonic waves to be transmitted or received is determined by the area of the vibration region. In particular, in transmission and reception of high-frequency ultrasonic waves, it is necessary to further reduce the area of the vibration region. On the other hand, as described above, in order to efficiently transmit and receive ultrasonic wave, it is necessary to set the vibration region to have a low aspect ratio. In the configuration disclosed in JP-A-2010-164331, in a case where the area of the vibration region is set to be small and a low aspect ratio is set, it is necessary to form the opening provided in the base portion very small. Accordingly, there is a problem that manufacturing is difficult and the mass productivity is lowered.

SUMMARY

An advantage of some aspects of the invention is to provide an ultrasonic transducer having high ultrasonic wave transmission and reception efficiency and excellent in mass productivity, an ultrasonic probe, an ultrasonic apparatus, an ultrasonic transducer manufacturing method, and a vibration device.

An ultrasonic transducer according to this application example includes: a substrate in which an opening is formed; a vibration film that is provided on the substrate so as to close the opening; a plurality of vibration elements that perform at least one of driving processing for driving the vibration film to vibrate and detection processing for detecting vibration of the vibration film and that are disposed at positions where the vibration film and the opening overlap each other in a plan view along a thickness direction of the vibration film; a support substrate that is disposed so as to face the vibration film, supports the vibration film, and has a surface facing the vibration film as a flat surface; and a suppressing portion that is provided between the adjacent vibration elements in the plan view, is bonded to both the vibration film and the support substrate, and is formed of a resin material for suppressing transmission of vibration of the vibration film.

According to this application example, the vibration film is provided on the substrate having an opening so as to close the opening, and a plurality of vibration elements are provided in a region where the opening and the vibration film overlap each other. Between the plurality of vibration elements of the vibration film, the suppressing portion formed of a resin material for suppressing the transmission of vibration of the vibration film is provided.

In such a configuration, in a case where a position (vibration region) where the vibration element is provided in the vibration film vibrates, the transmission of the vibration to a region other than the vibration region is suppressed by the suppressing portion. That is, even in a case where the opening is large, the aspect ratio of the vibration region can be set to a low aspect ratio by the suppressing portion. Accordingly, the distortion of the vibration film in the vibration region in the film thickness direction is increased. As a result, it is possible to output high-output (large sound pressure) ultrasonic waves at the time of driving processing by the vibration element (at the time of ultrasonic wave transmission), and it is possible to improve reception sensitivity at the time of detection processing by the vibration element (at the time of ultrasonic wave reception).

In addition, since this is a configuration in which a plurality of vibration elements are provided for one opening, it is possible to increase the size of the opening compared with, for example, a configuration in which one vibration element is provided for one opening. Therefore, since it is easy to form an opening, it is possible to obtain an ultrasonic transducer excellent in mass productivity.

In addition, since the suppressing portion is formed of a resin material, the vibration film and the support substrate can be easily bonded to each other by the suppressing portion using, for example, heat bonding. Therefore, it is possible to further improve the manufacturing efficiency. The suppressing portion formed of such a resin material can be formed on the vibration film easily and highly accurately by, for example, photolithography. That is, the suppressing portion can be accurately formed at a position corresponding to the vibration region corresponding to each vibration element in the vibration film. Accordingly, it is possible to suppress the inconvenience that the vibration of the vibration region is inhibited by the suppressing portion due to, for example, the shift of the position of the suppressing portion from the vibration region, it is possible to further improve the efficiency of transmission or reception.

In the ultrasonic transducer according to the application example, it is preferable that a connection wiring line connected to the vibration element is provided on the vibration film and that the suppressing portion contains a conductive filler and is connected to the connection wiring line.

In the application example with this configuration, the connection wiring line connected to the vibration element is provided on the vibration film, and is connected to the suppressing portion containing a conductive filler. In such a configuration, at a position close to the vibration element, it is possible to input and output signals from the suppressing portion to the vibration element. That is, in the related art, the connection wiring line of the vibration element is drawn out to the outer peripheral portion of the vibration film, and is connected to a terminal of an external circuit by, for example, a flexible printed circuit (FPC) or wire bonding. In this case, since the connection wiring line becomes long and the electric resistance increases, attenuation (voltage drop) of a signal input to and output from the vibration element occurs. In contrast, in the application example, since a signal can be input and output from the suppressing portion disposed at a position close to the vibration element as described above, it is possible to suppress a voltage drop. Therefore, it is possible to improve the driving efficiency of the ultrasonic transducer. That is, when transmitting ultrasonic waves from the ultrasonic transducer, ultrasonic waves having a desired output value can be appropriately output. In addition, in the case of receiving ultrasonic waves in the ultrasonic transducer, it is possible to acquire a received signal having a high signal value. Accordingly, it is possible to improve reception sensitivity.

In the ultrasonic transducer according to the application example, it is preferable that the support substrate has a wiring portion, which is connected to the suppressing portion, on a surface facing the vibration film.

In the application example with this configuration, the suppressing portion is connected to the wiring portion provided on the surface of the support substrate facing the vibration film. Therefore, by bonding the connection wiring line connected to the vibration element and the wiring portion to each other through the suppressing portion as described above, these can be electrically connected to each other.

In the ultrasonic transducer according to the application example, it is preferable that the support substrate includes a penetrating electrode that penetrates the support substrate in a thickness direction to connect the wiring portion and a circuit board, on which a circuit for controlling the vibration element is provided, to each other.

In the application example with this configuration, the penetrating electrode is further provided on the support substrate, and the penetrating electrode is connected to the wiring portion. Therefore, by connecting the penetrating electrode, which is exposed on the surface of the support substrate not facing the vibration film, to the circuit board, the vibration element can be easily electrically connected to the circuit board without using an FPC or the like.

An ultrasonic probe according to this application example includes: an ultrasonic transducer; and a housing in which the ultrasonic transducer is housed. The ultrasonic transducer includes: a substrate in which an opening is formed; a vibration film that is provided on the substrate so as to close the opening; a plurality of vibration elements that perform at least one of driving processing for driving the vibration film to vibrate and detection processing for detecting vibration of the vibration film and that are disposed at positions where the vibration film and the opening overlap each other in a plan view along a thickness direction of the vibration film; a support substrate that is disposed so as to face the vibration film, supports the vibration film, and has a surface facing the vibration film as a flat surface; and a suppressing portion that is provided between the adjacent vibration elements in the plan view, is bonded to both the vibration film and the support substrate, and is formed of a resin material for suppressing transmission of vibration of the vibration film.

The ultrasonic probe according to this application example includes the housing in which the ultrasonic transducer is housed as described above. As described above, the ultrasonic transducer has high ultrasonic wave transmission or reception efficiency, and is excellent in mass productivity. Therefore, it is possible to provide an ultrasonic probe having high ultrasonic wave transmission or reception efficiency and excellent in mass productivity.

An ultrasonic apparatus according to this application example includes: an ultrasonic transducer; and a control unit that controls the ultrasonic transducer. The ultrasonic transducer includes: a substrate in which an opening is formed; a vibration film that is provided on the substrate so as to close the opening; a plurality of vibration elements that perform at least one of driving processing for driving the vibration film to vibrate and detection processing for detecting vibration of the vibration film and that are disposed at positions where the vibration film and the opening overlap each other in a plan view along a thickness direction of the vibration film; a support substrate that is disposed so as to face the vibration film, supports the vibration film, and has a surface facing the vibration film as a flat surface; and a suppressing portion that is provided between the adjacent vibration elements in the plan view, is bonded to both the vibration film and the support substrate, and is formed of a resin material for suppressing transmission of vibration of the vibration film.

The ultrasonic apparatus according to this application example includes the ultrasonic transducer described above and the control unit that controls the ultrasonic transducer. As described above, since the ultrasonic transducer is excellent in mass productivity, it is also possible to improve the mass productivity in the ultrasonic apparatus. In addition, by controlling the ultrasonic transducer using the control unit, ultrasonic wave transmission processing or ultrasonic wave receiving processing in the ultrasonic transducer can be performed with high efficiency.

An ultrasonic transducer manufacturing method according to this application example includes: forming, on a vibration film of a substrate in which the vibration film is provided, a plurality of vibration elements for performing at least one of driving processing for driving the vibration film to vibrate and detection processing for detecting vibration of the vibration film; forming a suppressing portion, which is formed of a resin material for suppressing transmission of vibration of the vibration film, on a surface of the vibration film not facing the substrate and between the adjacent vibration elements in a plan view along a thickness direction of the vibration film; making a support substrate, which has a surface facing the vibration film as a flat surface, face the surface of the vibration film not facing the substrate and bonding the other end portion of the suppressing portion, which is on an opposite side to one end portion of the suppressing portion connected to the vibration film, to the support substrate by heating; and forming an opening in the substrate such that the plurality of vibration elements are disposed at positions where the vibration film and the opening overlap each other in the plan view.

In this application example, after forming the vibration elements on the vibration film of the substrate in which the vibration film is provided, the suppressing portion formed of a resin material is formed between the vibration elements on the vibration film. Then, in the bonding step, the suppressing portion formed of a resin material is heated to be bonded to the support substrate. Then, an opening is formed in the substrate.

In such a manufacturing method, since the suppressing portion formed of a resin material is formed on the vibration film, it is possible to form the suppressing portion between the vibration elements with high accuracy by photolithography or the like. Therefore, it is possible to form a vibration region at the desired position of the vibration film. Accordingly, it is possible to suppress a reduction in the efficiency of ultrasonic wave transmission and reception due to the positional shift between each vibration region and the vibration element. In addition, since the suppressing portion is bonded to the support substrate by heat bonding in the bonding step, it is not necessary to use an adhesive or the like. Accordingly, it is possible to improve the manufacturing efficiency. In addition, in the opening forming step, it is sufficient to form an opening over a plurality of vibration elements. Therefore, since it is possible to make the size of the opening relatively large, it is possible to further improve the manufacturing efficiency.

A vibration device according to this application example includes: a vibration film that has a predetermined thickness and is able to vibrate in a thickness direction; a support substrate that is disposed so as to face the vibration film, supports the vibration film, and has a surface facing the vibration film as a flat surface; and a suppressing portion that is provided along a vibration region in the vibration film and suppresses transmission of vibration of the vibration region of the vibration film to a region other than the vibration region. The suppressing portion is formed of a resin material, and is bonded to the vibration film and the support substrate.

In this application example, since the suppressing portion formed of a resin material is provided along the vibration region of the vibration film as described above, it is possible to suppress the transmission of vibration to a region other than the vibration region. Accordingly, it is possible to transmit and receive ultrasonic waves with high efficiency. In addition, since the suppressing portion formed of a resin material can be formed on the vibration film easily and highly accurately by, for example, photolithography, the suppressing portion can be easily bonded to the vibration film or to the support substrate by, for example, heat pressure bonding. Therefore, it is possible to improve the manufacturing efficiency of the ultrasonic transducer.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Hereinafter, a first embodiment will be described.

Figure 1:
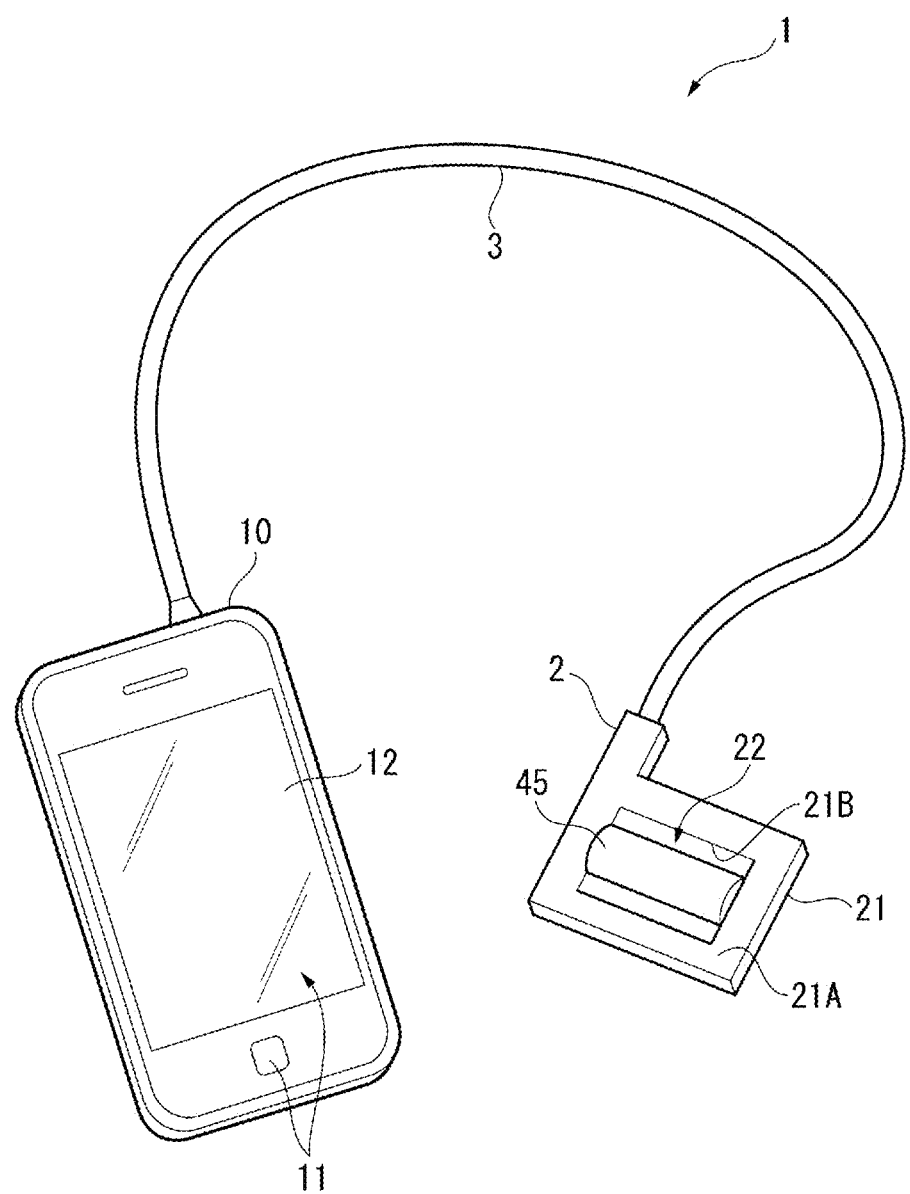
FIG. 1 is a diagram showing the schematic configuration of an ultrasonic measurement apparatus of a first embodiment.
Figure 2:
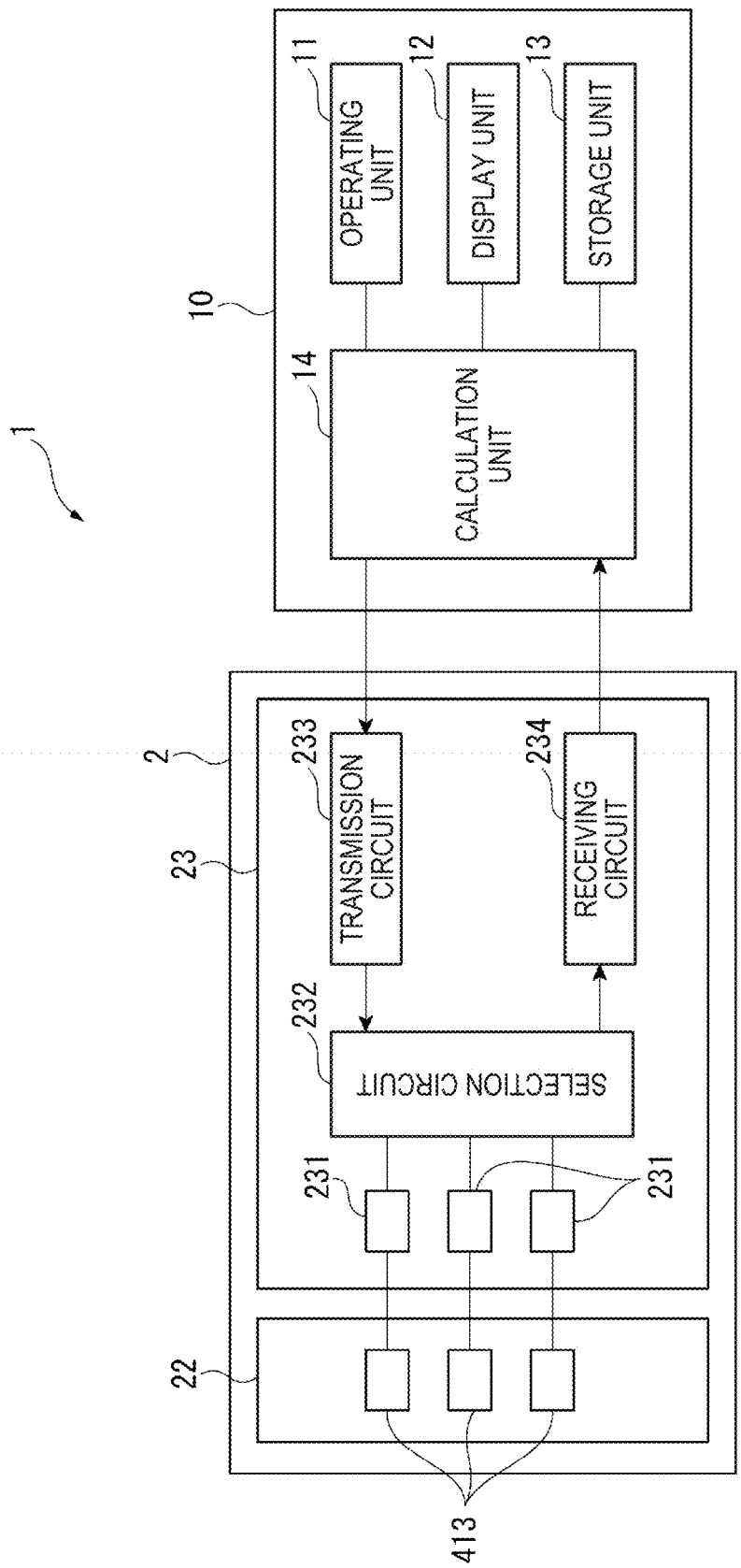
FIG. 2 is a block diagram showing the schematic configuration of the ultrasonic measurement apparatus of the first embodiment.

FIG. 1 is a diagram showing the schematic configuration of an ultrasonic measurement apparatus 1 of the first embodiment. FIG. 2 is a block diagram showing the schematic configuration of the ultrasonic measurement apparatus 1 of the present embodiment.

As shown in FIG. 1, the ultrasonic measurement apparatus 1 (ultrasonic apparatus) of the present embodiment includes an ultrasonic probe 2 and a control device 10 (control unit) that is electrically connected to the ultrasonic probe 2 through a cable 3.

In the ultrasonic measurement apparatus 1, the ultrasonic probe 2 is brought into contact with the surface of the living body (for example, a human body), ultrasonic waves are transmitted to the inside of the object (for example, a living body) from the ultrasonic probe 2, ultrasonic waves reflected by the organ in the living body are received by the ultrasonic probe 2, and, for example, an internal tomographic image in the living body is obtained or the state of the organ in the body (for example, a blood flow) is measured based on the received signal.

Configuration of an Ultrasonic Probe

The ultrasonic probe 2 includes a housing 21 (refer to FIG. 1), an ultrasonic sensor 22 provided in the housing 21, and a circuit board 23 on which a driver circuit for controlling the ultrasonic sensor 22 and the like are provided.

As shown in FIG. 1, the housing 21 is formed in a rectangular box shape in a plan view, for example. A sensor window 21B is provided on one surface (sensor surface 21A) perpendicular to the thickness direction, so that a part of the ultrasonic sensor 22 (ultrasonic transducer) housed thereinside is exposed. A passage hole of the cable 3 is provided in a part (in the example shown in FIG. 1, on a side surface) of the housing 21, and the cable 3 is connected to the circuit board 23 in the housing 21 through the passage hole. In addition, a gap between the cable 3 and the passage hole is filled with, for example, a resin material. Accordingly, waterproofness is ensured.

In the present embodiment, an example of the configuration is shown in which the ultrasonic probe 2 and the control device 10 are connected to each other using the cable 3. However, without being limited thereto, for example, the ultrasonic probe 2 and the control device 10 may be connected to each other by wireless communication, or various components of the control device 10 may be provided in the ultrasonic probe 2.

Configuration of an Ultrasonic Sensor

Figure 3:
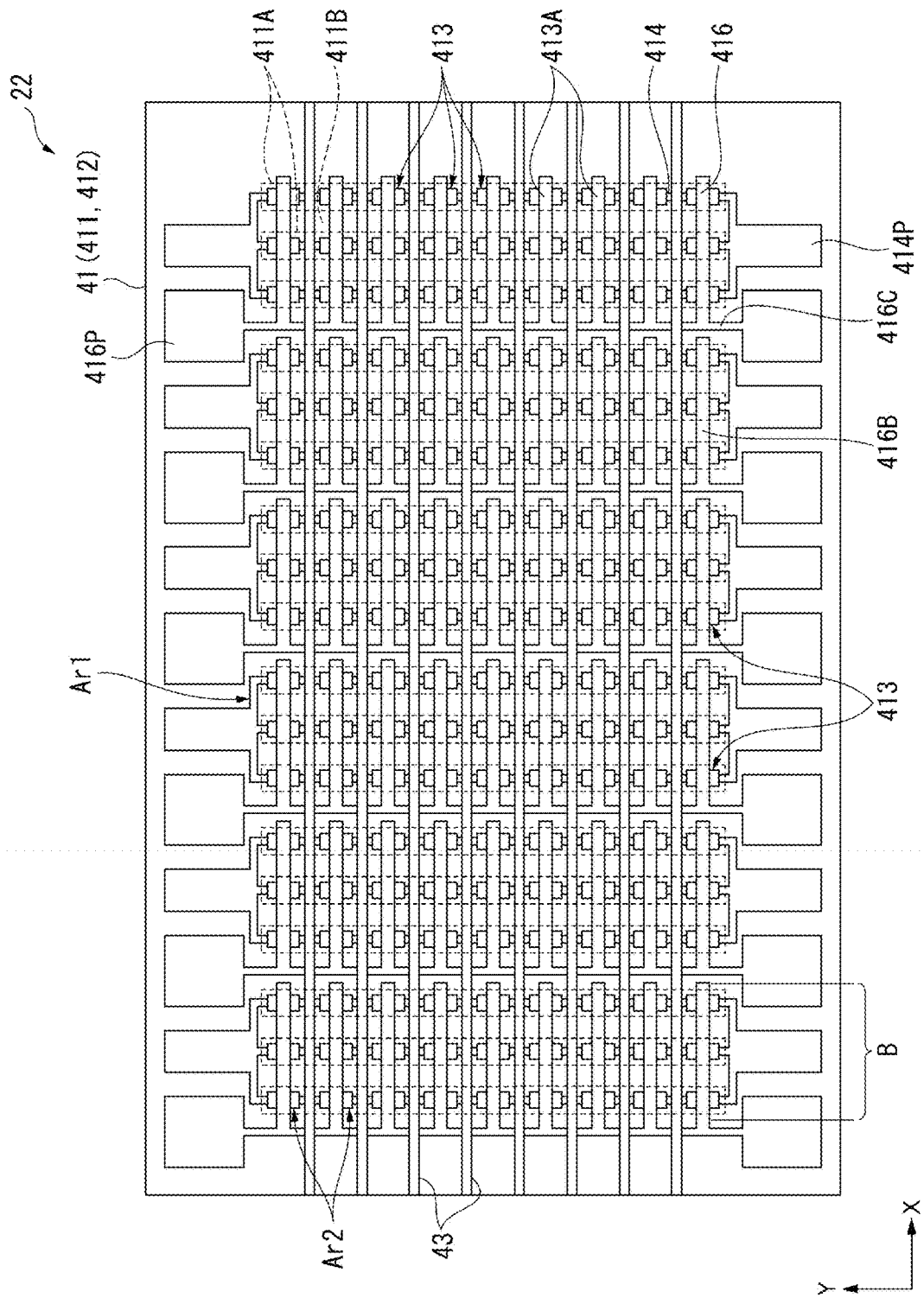
FIG. 3 is a plan view when a base portion in an ultrasonic sensor of the first embodiment is viewed from the sealing plate side.
Figure 4:
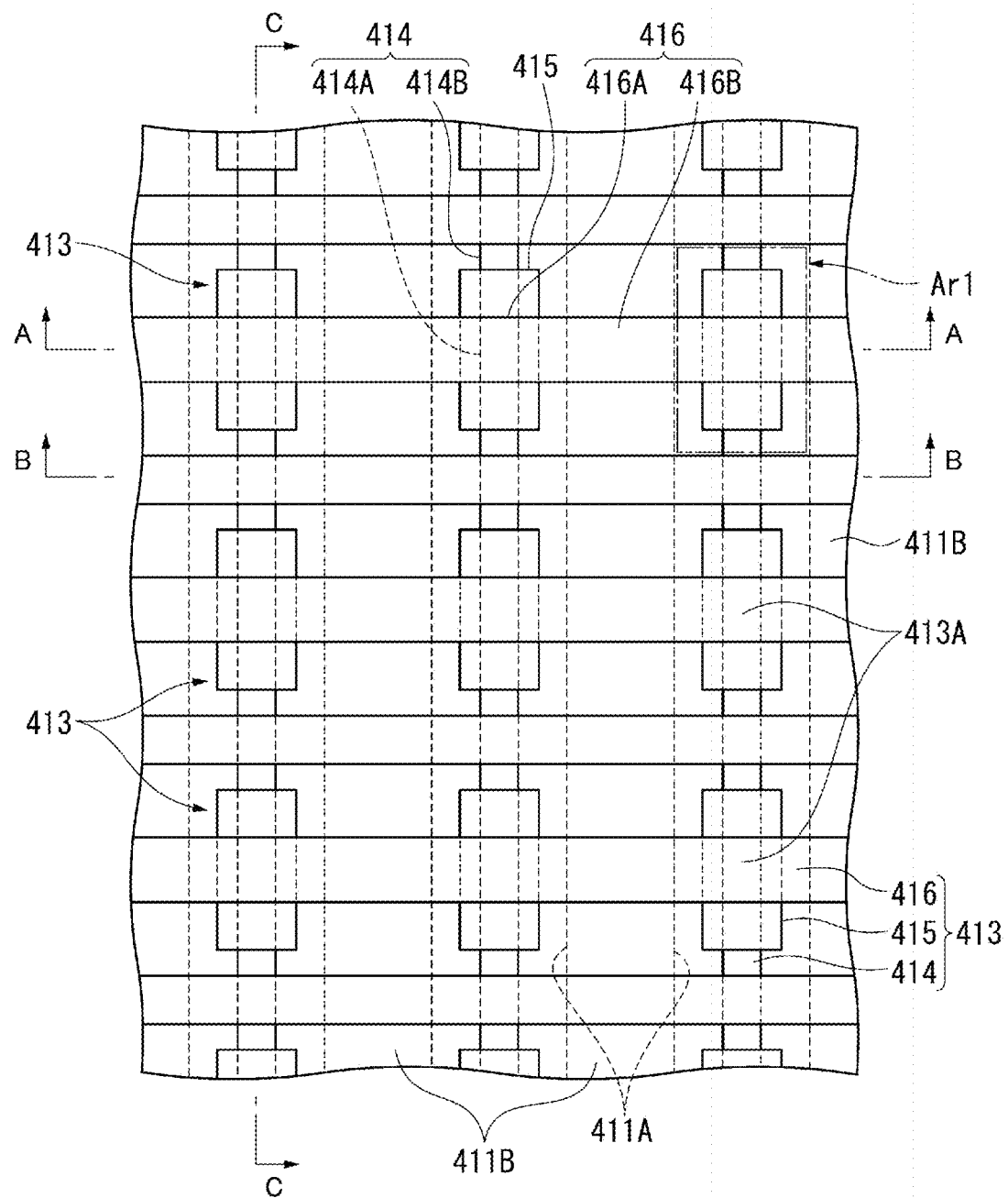
FIG. 4 is an enlarged plan view of a part of FIG. 3.
Figure 5A:
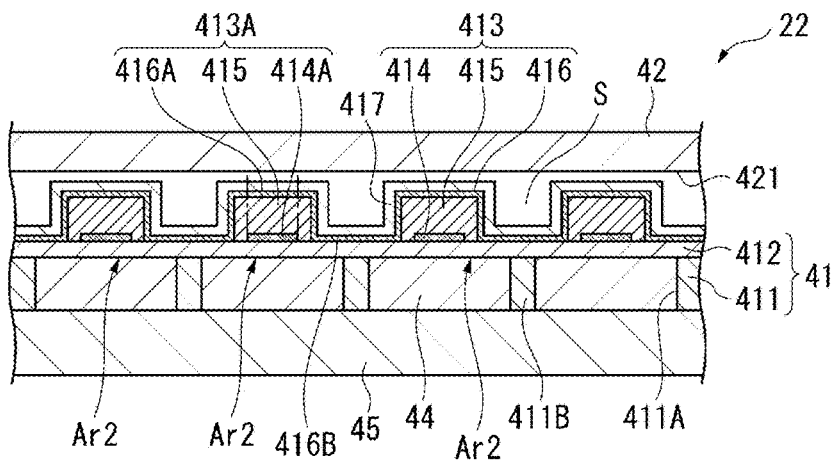
FIG. 5A is a sectional view of an ultrasonic sensor taken along the line A-A of FIG. 4.
Figure 5B:
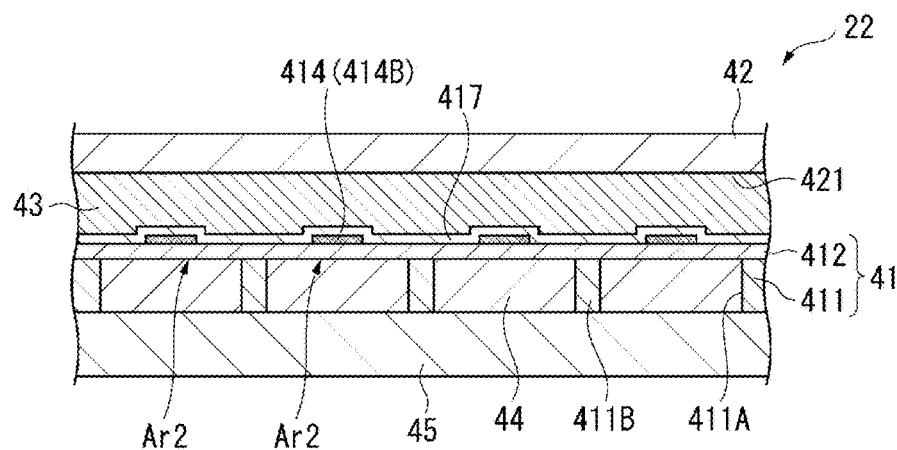
FIG. 5B is a sectional view of an ultrasonic sensor taken along the line B-B of FIG. 4.
Figure 5C:
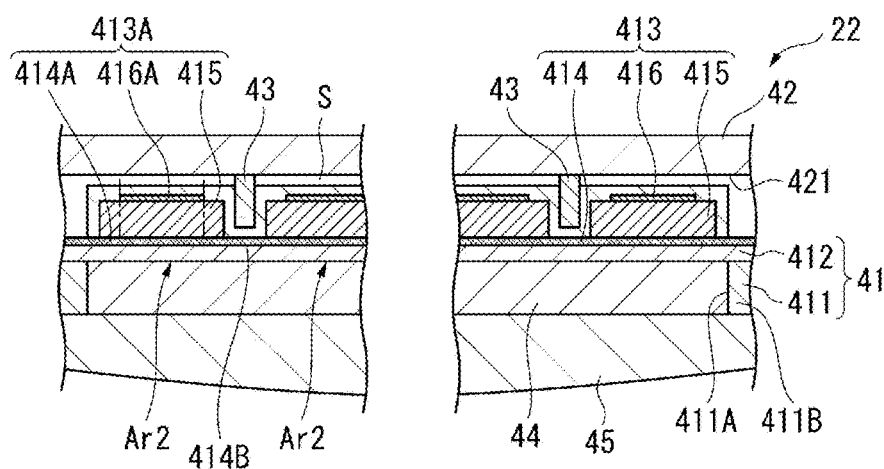
FIG. 5C is a sectional view of an ultrasonic sensor taken along the line C-C of FIG. 4.

FIG. 3 is a plan view when a base portion 41 in the ultrasonic sensor 22 is viewed from a sealing plate 42 side. FIG. 4 is an enlarged plan view of a part of FIG. 3. FIGS. 5A to 5C are sectional views of the ultrasonic sensor 22.

FIG. 5A is a sectional view taken along the line A-A of FIG. 4, FIG. 5B is a sectional view taken along the line B-B of FIG. 4, and FIG. 5C is a sectional view taken along the line C-C of FIG. 4.

As shown in FIG. 4, the ultrasonic sensor 22 (ultrasonic transducer) includes the base portion 41, the sealing plate 42 (support substrate), a suppressing portion 43, an acoustic matching layer 44, and an acoustic lens 45.

Configuration of a Base Portion

As shown in FIGS. 5A to 5C, the base portion 41 includes a substrate 411, a vibration film 412 laminated on the substrate 411, and a piezoelectric element 413 (vibration element) laminated on the vibration film 412.

Here, as shown in FIG. 3, in a plan view of the base portion 41 from the thickness direction, an array region Ar1 is provided at the center of the base portion 41, and a plurality of piezoelectric elements 413 are arranged in an array in the array region Ar1.

In addition, as shown in FIGS. 5A to 5C, the base portion 41 includes the substrate 411 in which an opening 411A is formed, the vibration film 412 provided on the back side of the substrate 411 so as to close the opening 411A, and the piezoelectric element 413 provided on a side of the vibration film 412 not facing the opening 411A.

Configuration of a Substrate

The substrate 411 is, for example, a semiconductor substrate formed of silicon (Si). In the array region Ar1 of the substrate 411, the opening 411A is provided as described above. The substrate 411 includes a partition wall 411B surrounding the opening 411A. As shown in FIGS. 3 to 5C, in a plan view of the vibration film 412 from the film thickness direction (Z direction), the opening 411A has a shape with a high aspect ratio in which the length along a second direction (Y direction) is much larger than the length along a first direction (X direction), for example, a shape with an aspect ratio of 1:70. On the other hand, in the piezoelectric element 413, an active portion 413A in which a lower electrode 414, a piezoelectric layer 415, and an upper electrode 416 are laminated has a shape with a low aspect ratio in which the length along the X direction is close to the length along the Y direction, for example, a shape with an aspect ratio of approximately 1. Taking into consideration that the distortion of the active portion 413A in the film thickness direction is increased, it can be said theoretically that it is the most ideal that the aspect ratio of the active portion 413A is 1. However, the aspect ratio of the active portion 413A may be a value larger than 1. For one opening 411A, a plurality of active portions 413A are arranged along the Y direction, for example.

Configuration of a Vibration Film

The vibration film 412 is a laminate formed of a silicon oxide ($SiO_2$) layer and a zirconium oxide ($ZrO_2$) layer, for example. The vibration film 412 is supported by the partition wall 411B of the substrate 411. The vibration film 412 closes the opening 411A provided in the substrate 411 as described above.

The thickness of the vibration film 412 is sufficiently smaller than the thickness of the substrate 411. In the present embodiment, in a region overlapping the opening 411A of the vibration film 412 that closes the opening 411A, a plurality of regions (vibration regions Ar2) surrounded by the partition wall 411B and the suppressing portion 43, which will be described later, are arranged along the Y direction. In the present embodiment, one active portion 413A is arranged in each of the vibration regions Ar2. The vibration region Ar2 is vibrated by the driving of the active portion 413A. Then, ultrasonic waves are transmitted, and the vibration region Ar2 vibrates. Then, a potential difference is generated in the piezoelectric layer 415 of the active portion 413A, and a detection signal is output. As a result, it is possible to detect the received ultrasonic waves.

Configuration of a Piezoelectric Element

The piezoelectric element 413 is provided on the vibration film 412, and is formed by the lower electrode 414, the piezoelectric layer 415, and the upper electrode 416. As described above, a portion in which the lower electrode 414, the piezoelectric layer 415, and the upper electrode 416 overlap each other in the film thickness direction (Z direction) functions as the active portion 413A of the piezoelectric element 413.

On the vibration film 412 or the piezoelectric element 413, an insulating layer 417 (protective layer) formed of, for example, alumina is formed.

The lower electrode 414 is patterned with a predetermined width in the X direction, and extends along the Y direction to be continuously provided over a plurality of active portions 413A. That is, the lower electrode 414 is formed by a lower electrode main body portion 414A, which forms a part of the active portion 413A, and a lower connection wiring line 414B that connects the lower electrode main body portions 414A adjacent to each other in the Y direction.

End portions of the plurality of lower electrodes 414 (in FIG. 3, for example, three lower electrodes 414) arranged in the Y direction are connected to each other. For example, the end portions of the plurality of lower electrodes 414 are drawn out to the peripheral ends of the substrate 411 on the ±Y sides, and a lower electrode terminal 414P is provided in a part (for example, a distal end) thereof. Although details will be described later, in the present embodiment, a block B of 1 channel (ch) is formed by the piezoelectric element 413 connected to the lower electrodes 414 that are connected to each other, and a plurality of blocks B are arranged in the X direction.

The upper electrode 416 is patterned with a predetermined width in the Y direction, and extends along the X direction to be continuously provided over a plurality of active portions 413A. That is, the upper electrode 416 is formed by an upper electrode main body portion 416A that forms a part of the active portion 413A, an upper connection wiring line 416B that connects the upper electrode main body portions 416A adjacent to each other in the X direction, and a common wiring line 416C that connects the upper connection wiring lines 416B to each other.

For example, as shown in FIG. 3, the common wiring line 416C is formed along the Y direction between the adjacent blocks B, and the common wiring line 416C is drawn out to the peripheral ends of the substrate 411 on the ±Y sides. An upper electrode terminal 416P is provided in a part (for example, a distal end) of the common wiring line 416C. Although an example in which the common wiring line 416C is disposed between the blocks B is shown in the present embodiment, for example, the end portions of the upper electrodes 416 may be connected to each other.

The piezoelectric layer 415 is disposed in a matrix corresponding to the intersection position of the lower electrode 414 and the upper electrode 416 in a plan view seen from the thickness direction of the vibration film 412.

Materials of the lower electrode 414 or the upper electrode 416 are not limited as long as the materials are conductive materials. As examples of the material of the lower electrode 414 or the upper electrode 416, it is possible to use metal materials such as platinum (Pt), iridium (Ir), gold (Au), aluminum (Al), copper (Cu), titanium (Ti), and stainless steel, tin oxide based conductive materials such as indium tin oxide (ITO) and fluorine doped tin oxide (FTC), zinc oxide based conductive materials, oxide conductive materials such as ruthenium acid strontium ($SrRuO_3$), nickel lanthanum ($LaNiO_3$), and earth doped strontium titanate, and a conductive polymer.

Typically, a composite oxide having a lead zirconate titanate (PZT) based perovskite structure ($ABO_3$-type structure) can be used as the piezoelectric layer 415. According to this, it becomes easy to ensure the amount of displacement of the piezoelectric element 413.

In addition, a composite oxide having a perovskite structure ($ABO_3$-type structure) containing no lead can be used as the piezoelectric layer 415. According to this, the ultrasonic sensor 22 can be realized using a non-lead-based material having a less influence on the environment.

As such a non-lead-based piezoelectric material, for example, a BFO-based material containing bismuth ferrite (BFO; $BiFeO_3$) can be mentioned. In BFO, Bi is located at A site, and iron (Fe) is located at B site. Other elements may be added to BFO. For example, at least one element selected from ferrate manganese (Mn), aluminum (Al), lanthanum (La), barium (Ba), titanium (Ti), cobalt (Co), cerium (Ce), samarium (Sm), chromium (Cr), potassium (K), lithium (Li), calcium (Ca), strontium (Sr), vanadium (V), niobium (Nb), tantalum (Ta), molybdenum (Mo), tungsten (W), nickel (Ni), zinc (Zn), praseodymium (Pr), neodymium (Nd), and Yuurobiumu (Eu) may be added to sodium potassium niobate (KNN; $KNaNbO_3$).

In addition, as another example of the non-lead-based piezoelectric material, a KNN-based material containing sodium potassium niobate (KNN) can be mentioned. Other elements may be added to KNN. For example, at least one element selected frommanganese (Mn), lithium (Li), barium (Ba), calcium (Ca), strontium (Sr), zirconium (Zr), titanium (Ti), bismuth (Bi), tantalum (Ta), antimony (Sb), iron (Fe), cobalt (Co), silver (Ag), magnesium (Mg), zinc (Zn), copper (Cu), vanadium (V), chromium (Cr), molybdenum (Mo), tungsten (W), nickel (Ni), aluminum (Al), silicon (Si), lanthanum (La), cerium (Ce), praseodymium (Pr), neodymium (Nd), promethium (Pm), samarium (Sm), and europium (Eu) may be added to KNN.

Examples of a composite oxide having a perovskite structure include a composite oxide deviating from the stoichiometric composition due to deficiency and excess or a composite oxide in which some elements have been replaced with other elements. That is, as long as the perovskite structure can be taken, not only inevitable deviation of composition due to lattice mismatch, oxygen deficiency, or the like but also substitution of some elements is allowed.

Configuration of a Sealing Plate and a Suppressing Portion

As shown in FIGS. 5A to 5C, the sealing plate 42 is disposed so as to face the vibration film 412 of the base portion 41.

The sealing plate 42 has a flat opposite surface 421 facing the vibration film 412, and the opposite surface 421 is bonded to the vibration film 412 of the base portion 41 by the suppressing portion 43 for suppressing the vibration of the vibration film 412. Since the sealing plate 42 is bonded to the base portion 41 by the suppressing portion 43, a space S around the piezoelectric element 413 is sealed.

In addition, since the material or thickness of the sealing plate 42 affects the frequency characteristics of the ultrasonic sensor 22, it is preferable to set the material or thickness of the sealing plate 42 based on the center frequency of ultrasonic waves transmitted and received by the ultrasonic sensor 22.

In the present embodiment, in the sealing plate 42, a through hole (not shown) is provided so as to face the lower electrode terminal 414P or the upper electrode terminal 416P. Through the through hole, a wiring portion (for example, an FPC) is connected to the lower electrode terminal 414P or the upper electrode terminal 416P of the base portion 41.

The suppressing portion 43 is formed of a resin material, and is bonded to both the vibration film 412 of the base portion 41 and the sealing plate 42 as described above. The suppressing portion 43 is formed on the vibration film 412 by, for example, sputtering and is patterned, and is then bonded to the sealing plate 42 by heat bonding.

As shown in FIGS. 3 to 5C, the suppressing portion 43 is disposed at the midpoint position of the adjacent active portions 413A between the active portions 413A of the piezoelectric elements 413 arranged in the Y direction, and is formed so as to extend along the X direction.

That is, the partition wall 411B is present between each vibration region Ar2 of the vibration film 412 and the vibration region Ar2 adjacent thereto in the X direction. Accordingly, as shown in FIGS. 5A and 5B, sides of each vibration region Ar2 parallel to the Y direction (portions on both outer sides of the sides of each active portion 413A parallel to the Y direction) are fixed by the partition wall 411B. On the other hand, as shown in FIG. 5C, in the Y direction, between the adjacent vibration regions Ar2, there is a portion where the partition wall 411B is not present. The suppressing portion 43 is provided in the portion. In addition, on sides of each vibration region Ar2 parallel to the X direction (portions on both outer sides of the sides of each active portion 413A parallel to the X direction), the vibration film 412 is fixed by the suppressing portion 43 or the partition wall 411B of the substrate 411.

Configuration of an Acoustic Matching Layer and an Acoustic Lens

As shown in FIGS. 5A to 5C, the acoustic matching layer 44 is provided on the working surface (not facing the sealing plate 42) side of the base portion 41. Specifically, the acoustic matching layer 44 is filled in the opening 411A of the base portion 41, and is formed in a predetermined thickness from the working surface side of the substrate 411.

The acoustic lens 45 is provided on the acoustic matching layer 44, and is exposed to the outside from the sensor window 21B of the housing 21 as shown in FIG. 1.

Due to the acoustic matching layer 44 or the acoustic lens 45, ultrasonic waves transmitted from the ultrasonic sensor 22 efficiently propagate toward the living body that is a measurement target, and ultrasonic waves reflected from the inside of the living body efficiently propagate toward the ultrasonic sensor 22. For this reason, the acoustic impedance of the acoustic matching layer 44 and the acoustic lens 45 is set to the intermediate acoustic impedance between the acoustic impedance of the ultrasonic sensor 22 and the acoustic impedance of the living body.

Transmission and Reception of Ultrasonic Waves by an Ultrasonic Sensor

In the ultrasonic sensor 22 described above, the upper electrodes 416 of the respective piezoelectric elements 413 arranged in the array region Ar1 are connected to each other. Therefore, the upper electrodes 416 of the respective piezoelectric elements 413 arranged in the array region Ar1 have the same electric potential. Assuming that the piezoelectric elements 413 along the Y direction are a group of piezoelectric elements, the lower electrodes 414 of the piezoelectric elements 413 included in three groups of piezoelectric elements along the X direction are connected to each other.

Therefore, the lower electrodes 414 of the piezoelectric elements 413 included in three groups of piezoelectric elements along the X direction have the same electric potential. In the present embodiment, a plurality of blocks B are arranged along the X direction with the three groups of piezoelectric elements as the block B of 1 channel (ch).

Then, in the present embodiment, at the time of transmission (driving processing) of ultrasonic waves, a driving signal SIG is input to each lower electrode terminal 414P, and a common bias signal COM is input to each upper electrode terminal 416P from the circuit board 23. By controlling the strength or the input timing of the driving signal input to each lower electrode terminal 414P, a potential difference is generated between the lower electrode 414 and the upper electrode 416 of each active portion 413A included in each block B, and the piezoelectric layer 415 vibrates. Accordingly, the vibration region Ar2 of the vibration film 412 is also driven to vibrate. As a result, ultrasonic waves are generated.

At the time of reception (detection processing) of ultrasonic waves, a common bias signal is input to the upper electrode terminal 416P from the circuit board 23. Then, ultrasonic waves from an object are input to the ultrasonic sensor 22, and each vibration region Ar2 of the vibration film 412 is driven to vibrate. Accordingly, a potential difference is generated between the lower electrode 414 and the upper electrode 416. Then, a detection signal corresponding to the deflection of the piezoelectric element 413 is output to the circuit board 23 from the lower electrode terminal 414P corresponding to each block B.

Since the ease of deflection deformation of the piezoelectric element 413 changes with the material or thickness of the piezoelectric element 413 or the vibration film 412 and the arrangement position or size of the vibration region Ar2, it is possible to appropriately adjust the material or thickness of the piezoelectric element 413 or the vibration film 412 and the arrangement position or size of the vibration region Ar2 according to the application or usage mode.

In addition, using a resonance frequency unique to each material, the resonance frequency and the frequency of a charge signal applied to the piezoelectric element 413 may be made to match or substantially match each other to cause the deflection deformation of the piezoelectric element 413 using resonance.

Figure 6A:
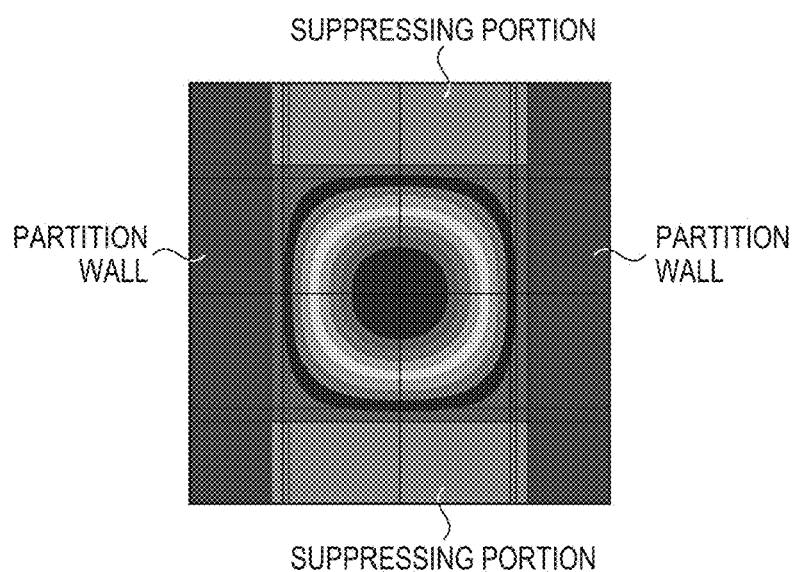
FIG. 6A is a diagram showing a displacement profile of a vibration film in the first embodiment.
Figure 6B:
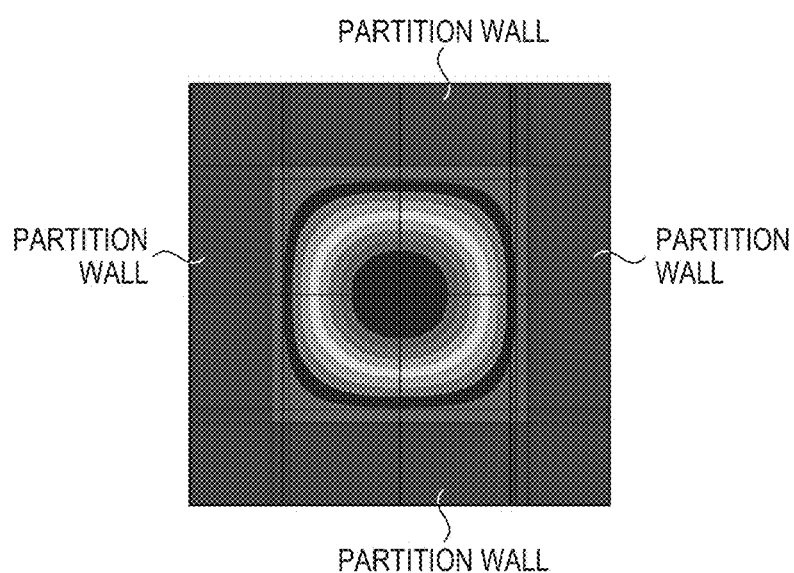
FIG. 6B is a diagram showing a displacement profile of a known vibration film (a vibration region is formed by only a partition wall)
Figure 6C:
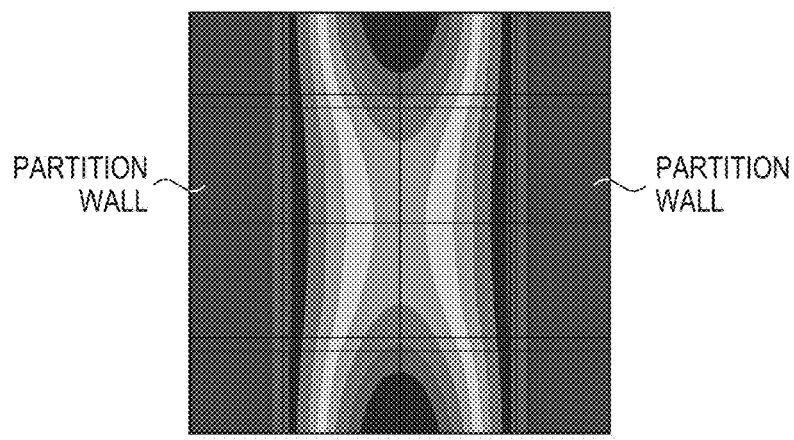
FIG. 6C is a diagram showing a displacement profile in a case where no suppressing portion is provided.

Displacement of a Vibration Film at the Time of Transmission and Reception of Ultrasonic Waves FIG. 6A is a diagram showing a displacement profile of a vibration film in the present embodiment, FIG. 6B is a diagram showing a displacement profile of a known vibration film (in the related art, a vibration region is formed by only a partition wall), and FIG. 6C is a diagram showing a displacement profile in a case where no suppressing portion is provided in the present embodiment.

As described above, in the present embodiment, when transmitting ultrasonic waves from the ultrasonic sensor 22 and when receiving ultrasonic waves, each vibration region Ar2 of the vibration film 412 is displaced.

In the case of the displacement profile of the vibration region Ar2 of the present embodiment, as shown in FIG. 6A, the center of the vibration region Ar2 (the center of the active portion 413A) is the center of the displacement, and large displacement (distortion in the film thickness direction) occurs in the vibration region Ar2. This is almost the same as in the case shown in FIG. 6B in which a substrate having an opening with a low aspect ratio is used (case where the vibration region Ar2 is formed by only the partition wall 411B). On the other hand, in a case where the suppressing portion 43 is not provided, as shown in FIG. 6C, the center of the displacement moves to the outside of the active portion 413A. Accordingly, the displacement (distortion in the film thickness direction) of the active portion 413A is considerably small.

From FIGS. 6A to 6C, it can be seen that, in a case where there is a portion where the partition wall 411B is not present between the adjacent active portions 413A (midpoint position), it is possible to suppress the vibration of the vibration film 412 by providing the suppressing portion 43 in the portion and pressing the vibration film 412 against the substrate 411 from the side opposite to the opening 411A. That is, it can be seen that the vibration range of the vibration film 412 is restricted by the suppressing portion 43. In addition, in the present embodiment, although the opening 411A has a high aspect ratio, the same displacement as in the case where the opening 411A has a low aspect ratio is obtained. Therefore, it can be seen that the effect of suppressing vibration using the suppressing portion 43 is enormous.

Configuration of a Circuit Board

As shown in FIG. 2, the circuit board 23 has a substrate terminal portion 231 connected to the lower electrode terminal 414P or the upper electrode terminal 416P provided in the base portion 41. In addition, a driver circuit for driving the ultrasonic sensor 22 and the like are provided on the circuit board 23. Specifically, as shown in FIG. 2, the circuit board 23 includes a selection circuit 232, a transmission circuit 233, a receiving circuit 234, and the like.

The selection circuit 232 switches a transmission connection for connecting the ultrasonic sensor 22 and the transmission circuit 233 and a reception connection for connecting the ultrasonic sensor 22 and the receiving circuit 234 based on the control of the control device 10.

When switching to the transmission connection is made by the control of the control device 10, the transmission circuit 233 outputs a signal, which indicates the transmission of ultrasonic waves, to the ultrasonic sensor 22 through the selection circuit 232.

When switching to the reception connection is made by the control of the control device 10, the receiving circuit 234 outputs a detection signal, which is input from the ultrasonic sensor 22 through the selection circuit 232, to the control device 10. The receiving circuit 234 is configured to include, for example, a low noise amplifier circuit, a voltage controlled attenuator, a programmable gain amplifier, a low pass filter, and an A/D converter. The receiving circuit 234 performs various kinds of signal processing, such as the conversion of a received signal to a digital signal, removal of noise components, and amplification to a desired signal level, and then outputs the received signal after the processing to the control device 10.

Configuration of a Control Device

As shown in FIG. 2, the control device 10 is configured to include, for example, an operating unit 11, a display unit 12, a storage unit 13, and a calculation unit 14. As examples of the control device 10, a terminal device, such as a tablet terminal, a smartphone, or a personal computer, may be used, or a dedicated terminal device for operating the ultrasonic probe 2 may be used.

The operating unit 11 is a user interface (UI) used when the user operates the ultrasonic measurement apparatus 1. For example, the operating unit 11 can be configured to include a touch panel provided on the display unit 12, operation buttons, a keyboard, a mouse, or the like.

The display unit 12 is formed using, for example, a liquid crystal display, and displays an image thereon.

The storage unit 13 stores various programs and various kinds of data for controlling the ultrasonic measurement apparatus 1.

The calculation unit 14 is configured to include, for example, an arithmetic circuit, such as a central processing unit (CPU), and a storage circuit, such as a memory. The calculation unit 14 reads various programs stored in the storage unit 13 and executes the various programs, thereby performing the generation of a transmission signal and the control of output processing for the transmission circuit 233 and performing received signal frequency setting, gain setting, or the like for the receiving circuit 234.

Method of Manufacturing an Ultrasonic Sensor

Next, a method of manufacturing the above ultrasonic sensor 22 will be described.

Figure 7:
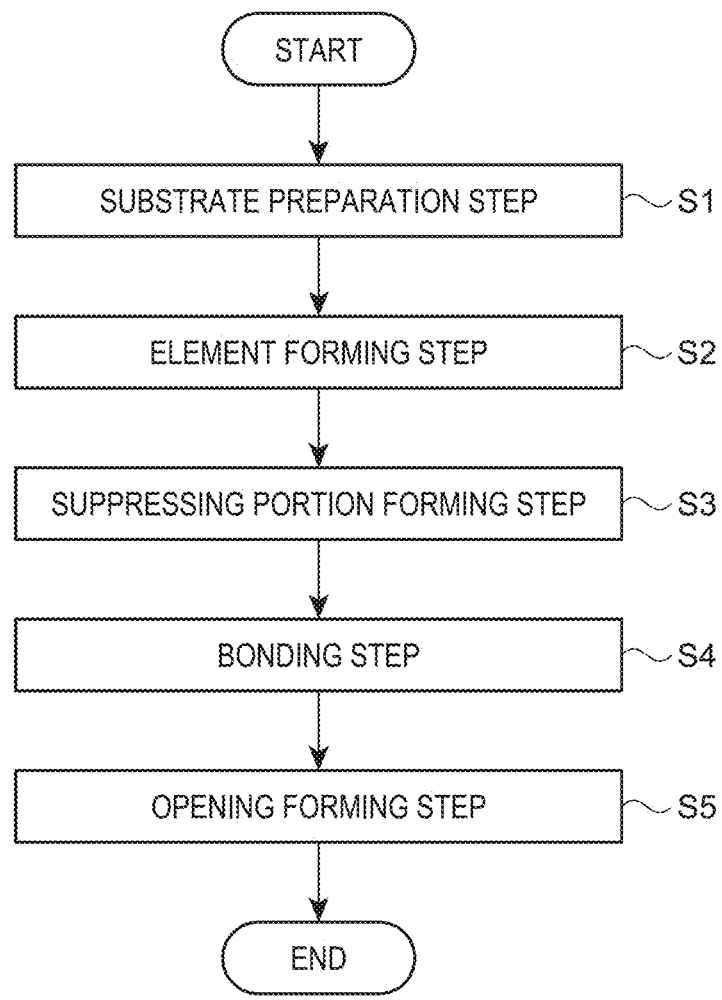
FIG. 7 is a flowchart showing a method of manufacturing the ultrasonic sensor of the first embodiment.

FIG. 7 is a flowchart showing each step in the manufacturing of the ultrasonic sensor 22 of the present embodiment. FIGS. 8A to 8F are diagrams schematically showing the ultrasonic sensor 22 in each step.

In order to manufacture the ultrasonic sensor 22, as shown in FIG. 7, a substrate preparation step S1, an element forming step S2, a suppressing portion forming step S3, a bonding step S4, and an opening forming step S5 are performed.

Figure 8A:
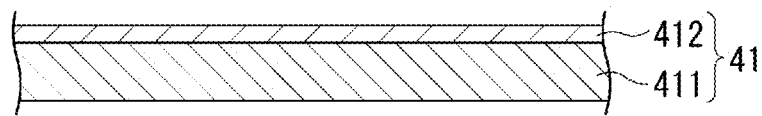
FIGS. 8A to 8F are diagrams showing the state of the ultrasonic sensor in each step of FIG. 7.

In the substrate preparation step S1, first, one surface side of the substrate 411 formed of Si is thermally oxidized to form an SiO$_2$ layer that is a part of the vibration film 412. Then, a Zr layer is formed on the SiO$_2$ layer, and the Zr layer is thermally oxidized to form a ZrO$_2$ layer. As a result, as shown in FIG. 8A, the vibration film 412 is formed on the substrate 411.

Then, the element forming step S2 is performed.

In the element forming step S2, first, an electrode material for forming the lower electrode 414 is formed on the vibration film 412 by sputtering, for example. Then, a resist is applied on the lower electrode 414, a resist pattern is formed by photolithography or the like, and the lower electrode 414 is patterned by etching, for example.

Then, the piezoelectric layer 415 is formed on the lower electrode 414. The piezoelectric layer 415 is formed by a solution method using PZT, for example. For example, application processing for applying the PZT solution with a composition ratio of Zr:Ti=52:48 on the vibration film 412 and the lower electrode 414 and baking processing for baking the applied PZT solution under the conditions of, for example, pre-baking of 400° C. and RTA baking of 700° C. are performed multiple times, thereby obtaining a piezoelectric layer having a desired thickness. Then, the piezoelectric layer 415 is formed by patterning the formed piezoelectric layer by etching (ion milling).

After forming the piezoelectric layer 415, an electrode material for forming the upper electrode 416 is applied on the vibration film 412. Then, in the same manner as for the lower electrode 414, a resist pattern is formed and patterned by etching or the like.

Figure 8B:
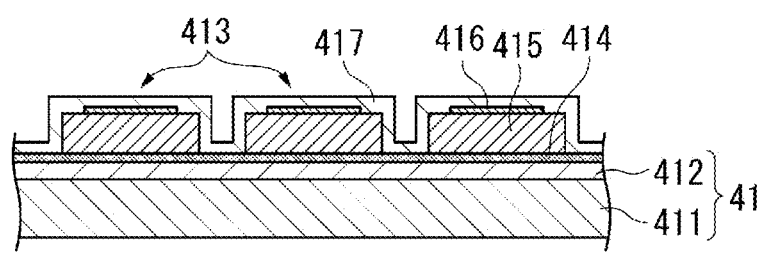

Thus, as shown in FIG. 8B, the piezoelectric element 413 configured to include the lower electrode 414, the piezoelectric layer 415, and the upper electrode 416 is formed on the vibration film 412. In the present embodiment, the thickness of the active portion 413A is set to about 1.3 μm.

After forming the piezoelectric element 413, the insulating layer 417 that covers the vibration film 412 and the piezoelectric element 413 is formed as a protective layer. The insulating layer 417 on the lower electrode terminal 414P and the upper electrode terminal 416P is removed by etching or the like.

Then, the suppressing portion 43 is formed on the vibration film 412 (on the insulating layer 417).

Figure 8C:
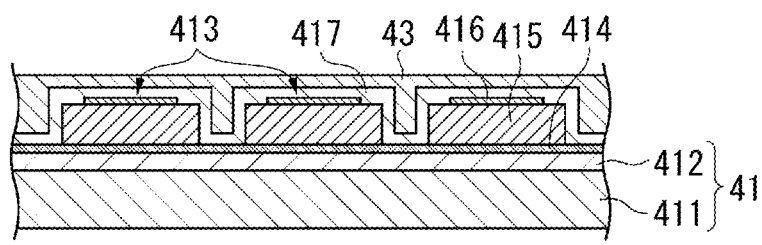
Figure 8D:
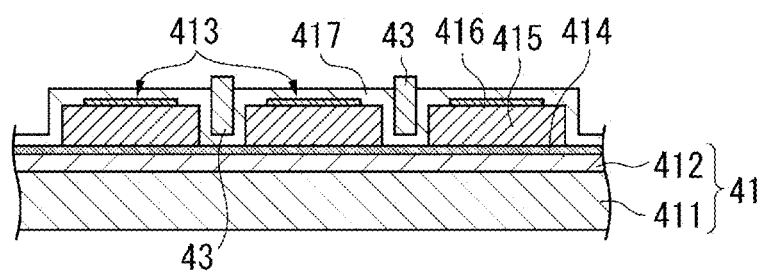

In forming the suppressing portion 43, as shown in FIG. 8C, for example, a photosensitive resin material (photoresist) is applied onto the vibration film 412 by spin coating, sputtering, or the like. Then, on the vibration film 412, a mask pattern along the X direction is formed between the active portions 413A. A region other than the mask is removed by photolithography. As a result, as shown in FIG. 8D, the suppressing portion 43 formed of a resin material is formed on the vibration film 412.

Figure 8E:
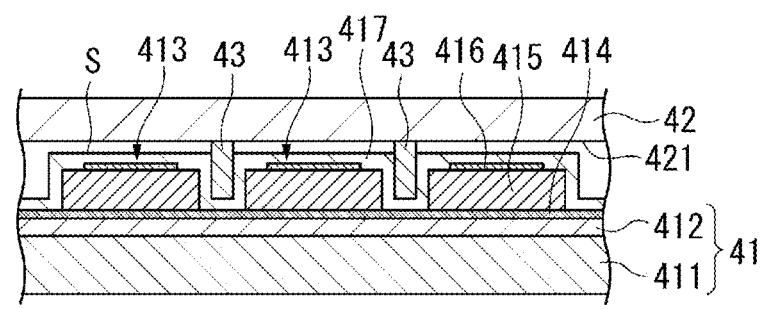

Then, the bonding step S4 is performed. In the bonding step S4, the substrate 411 is placed on, for example, a hot plate (not shown) so that the vibration film 412 faces upward (side opposite to the hot plate). In addition, the sealing plate 42 is placed on the vibration film 412, and the sealing plate 42 is pressed toward the substrate 411 side with predetermined pressure. Then, the suppressing portion 43 that is a resin material is softened. As a result, as shown in FIG. 8E, an end portion of the suppressing portion 43 not facing the vibration film 412 is heated to be bonded (melted to be bonded) to the sealing plate 42. The thickness of the suppressing portion 43 along the Z direction in the bonding state is, for example, about 1.5 μm, which is sufficiently larger than the width of the suppressing portion 43 in the Y direction. Therefore, for example, in the ultrasonic sensor 22 for living body, the suppressing portion 43 is not deformed or crushed even if normal pressure is applied. As a result, it is possible to suppress the deformation of the vibration film 412 and the like.

In the present embodiment, the suppressing portion 43 of a resin material is formed on the vibration film 412 by photolithography. In such a case, for example, compared with a case where the suppressing portion 43 is provided on the sealing plate 42 side, it is possible to improve the positional accuracy of the suppressing portion 43.

That is, in a case where the suppressing portion 43 is provided on the sealing plate 42 and the distal end is bonded to the vibration film 412, it is necessary to perform alignment so that the suppressing portion 43 is located at the intermediate position of the active portion 413A of the piezoelectric element 413. When the suppressing portion 43 is in contact with the active portion 413A, the driving efficiency of the active portion 413A is reduced. Accordingly, the sound pressure of ultrasonic waves is reduced in ultrasonic wave transmission processing, and reception sensitivity is reduced in ultrasonic wave reception processing. Even if the suppressing portion 43 is not in contact with the active portion 413A, if the position is shifted, a deviation occurs in the shape or size of the vibration region Ar2. Accordingly, since it becomes difficult to transmit and receive ultrasonic waves having a desired frequency, the driving efficiency of the active portion 413A is reduced, and the efficiency in ultrasonic wave transmission and reception is also reduced.

In contrast, in the present embodiment, the suppressing portion 43 is patterned on the vibration film 412 by photolithography as described above. Therefore, it is possible to form the suppressing portion 43 at an optimal position with respect to the active portion 413A or the vibration region Ar2. That is, since it is possible to form the accurate ultrasonic sensor 22, complicated alignment is not necessary. Therefore, it is possible to improve the manufacturing efficiency.

The suppressing portion 43 formed of a resin material can be easily bonded to the sealing plate 42 by heat bonding as described above. In a case where apart of the sealing plate 42 is protruded to form the suppressing portion 43 or a case where the suppressing portion 43 is formed of a metal material or the like, it is necessary to bond the suppressing portion 43 to the vibration film 412 by separately applying an adhesive or the like. Accordingly, the time and effort is the bonding step are increased. In addition to the complication of alignment described above, there is a possibility that the adhesive will adhere to the active portion 413A. In contrast, in the present embodiment, the sealing plate 42 and the vibration film 412 can be bonded to each other easily.

Figure 8F:
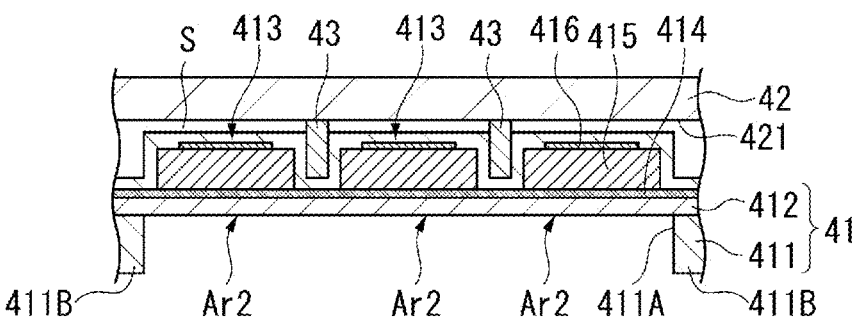

Thus, after bonding the sealing plate 42 to the base portion 41, the opening forming step S5 is performed. In the opening forming step S5, from the surface of the substrate 411 not facing the vibration film 412, the opening 411A is formed by, for example, etching, as shown in FIG. 8F. Specifically, a mask is formed in a region other than the formation region of the opening 411A, and the opening 411A is formed using the $SiO_2$ layer of the vibration film 412 as an etching stopper. In the case of bonding the suppressing portion 43 and the sealing plate 42 to each other after forming the opening 411A, the vibration film 412 is deformed when the sealing plate 42 is pressed toward the base portion 41 side. In contrast, in the present embodiment, the opening 411A is formed after bonding the sealing plate 42 to the vibration film 412. Therefore, it is possible to suppress the deformation of the vibration film 412 due to pressing by the suppressing portion 43.

Then, the opening 411A of the substrate 411 is filled with the acoustic matching layer 44, and the acoustic lens 45 is further bonded thereto, thereby manufacturing the ultrasonic sensor 22 shown in FIGS. 5A to 5C and the like.

Effect of the Present Embodiment

The ultrasonic measurement apparatus 1 of the present embodiment includes the ultrasonic probe 2, in which the ultrasonic sensor 22 for transmitting and receiving ultrasonic waves is disposed in the housing 21, and the control device 10 for controlling the ultrasonic sensor 22. The ultrasonic sensor 22 includes the substrate 411 having the opening 411A, the vibration film 412 that closes the opening 411A, the piezoelectric element 413 provided on the vibration film 412, and the sealing plate 42 that has the opposite surface 421, which is a flat surface facing the vibration film 412, and supports the vibration film 412. In addition, a plurality of piezoelectric elements 413 (active portions 413A) are provided at positions overlapping the opening 411A in a plan view, and the suppressing portion 43 formed of a resin material for suppressing the transmission of vibration of the vibration film 412 is provided between the adjacent active portions 413A.

In such a configuration, the vibration film 412 is divided into a plurality of vibration regions Ar2 by the partition wall 411B and the suppressing portion 43, and the active portion 413A of the piezoelectric element 413 is located at the center of each vibration region Ar2. Accordingly, even in a case where the opening 411A is large, the aspect ratio of each vibration region Ar2 can be reduced to a low aspect ratio.

In addition, as shown in FIGS. 6A to 6C, transmission of vibration of each vibration region Ar2 to a region (for example, the adjacent vibration region Ar2) other than the vibration region Ar2 is suppressed by the suppressing portion 43, and the amount of distortion in the thickness direction is increased at the center position of each vibration region Ar2 where the active portion 413A is provided. Therefore, high-output (large sound pressure) ultrasonic waves can be output when transmitting ultrasonic waves, and reception sensitivity can be improved when receiving ultrasonic waves (efficiency of transmission and reception of ultrasonic waves is improved).

In addition, for example, compared with a case where one active portion 413A is disposed for one opening 411A, it is possible to increase the size of the opening 411A. Accordingly, since it is easy to form the opening 411A, it is possible to improve the mass productivity of the ultrasonic sensor 22.

The suppressing portion 43 formed of such a resin material can be easily formed by, for example, photolithography, and can be easily bonded to the sealing plate 42 by heat bonding. Accordingly, since it is possible to further improve the manufacturing efficiency of the ultrasonic sensor 22, it is possible to further improve the mass productivity of the ultrasonic sensor 22.

In the present embodiment, after the substrate preparation step S1 and the element forming step S2, in the suppressing portion forming step, the suppressing portion 43 is formed by forming a photosensitive resin material layer on the vibration film 412 and patterning the photosensitive resin material layer by photolithography. Therefore, since it is possible to further improve the manufacturing efficiency, it is also possible to improve the efficiency in ultrasonic wave transmission and reception of the ultrasonic sensor 22.

That is, in a configuration in which a protruding portion provided on the sealing plate side is bonded to the vibration as a suppressing portion, it is necessary to align the position of the protruding portion highly accurately with respect to the opening 411A or the active portion 413A so that the active portion 413A is located at the center position of the vibration region Ar2. For this reason, the manufacturing efficiency is reduced. In addition, if the position of the protruding portion is shifted, the vibration region Ar2 cannot be formed at a desired position. Accordingly, a positional shift between the active portion 413A and the center of the vibration region Ar2 where the amount of distortion in the film thickness direction is the greatest occurs. In this case, the efficiency in ultrasonic wave transmission and reception is reduced.

In addition, since it is necessary to bond the protruding portion with an adhesive, a step of transferring the adhesive to the vibration film 412 is further required. In this case, there is a possibility that the transferred adhesive will overflow to the piezoelectric element 413 side to come into contact with the piezoelectric element 413 at the time of bonding. This may inhibit the driving of the piezoelectric element 413.

In contrast, in the present embodiment, the suppressing portion 43 formed of a resin material is formed by photolithography in the above suppressing portion forming step S3, and the suppressing portion 43 and the sealing plate 42 are bonded to each other by heat bonding in the bonding step S4. In this case, since it is possible to omit the step of transferring an adhesive or the alignment step described above, the manufacturing efficiency is further improved to the same extent. In addition, since the suppressing portion 43 can be formed at a desired position with high accuracy by photolithography, it is possible to arrange the vibration region Ar2 at a desired position. As a result, it is possible to suppress a reduction in the efficiency of ultrasonic wave transmission and reception.

Second Embodiment

Next, a second embodiment will be described.
In the first embodiment described above, the lower electrode 414 and the upper electrode 416 extend to the lower electrode terminal 414P and the upper electrode terminal 416P provided in the outer peripheral portion of the substrate 411, thereby being connected to the circuit board 23 at the lower electrode terminal 414P and the upper electrode terminal 416P, respectively. In contrast, the second embodiment is different from the first embodiment in that the lower electrode 414 and the upper electrode 416 are connected to the circuit board 23 through a suppressing portion.

Figure 9:
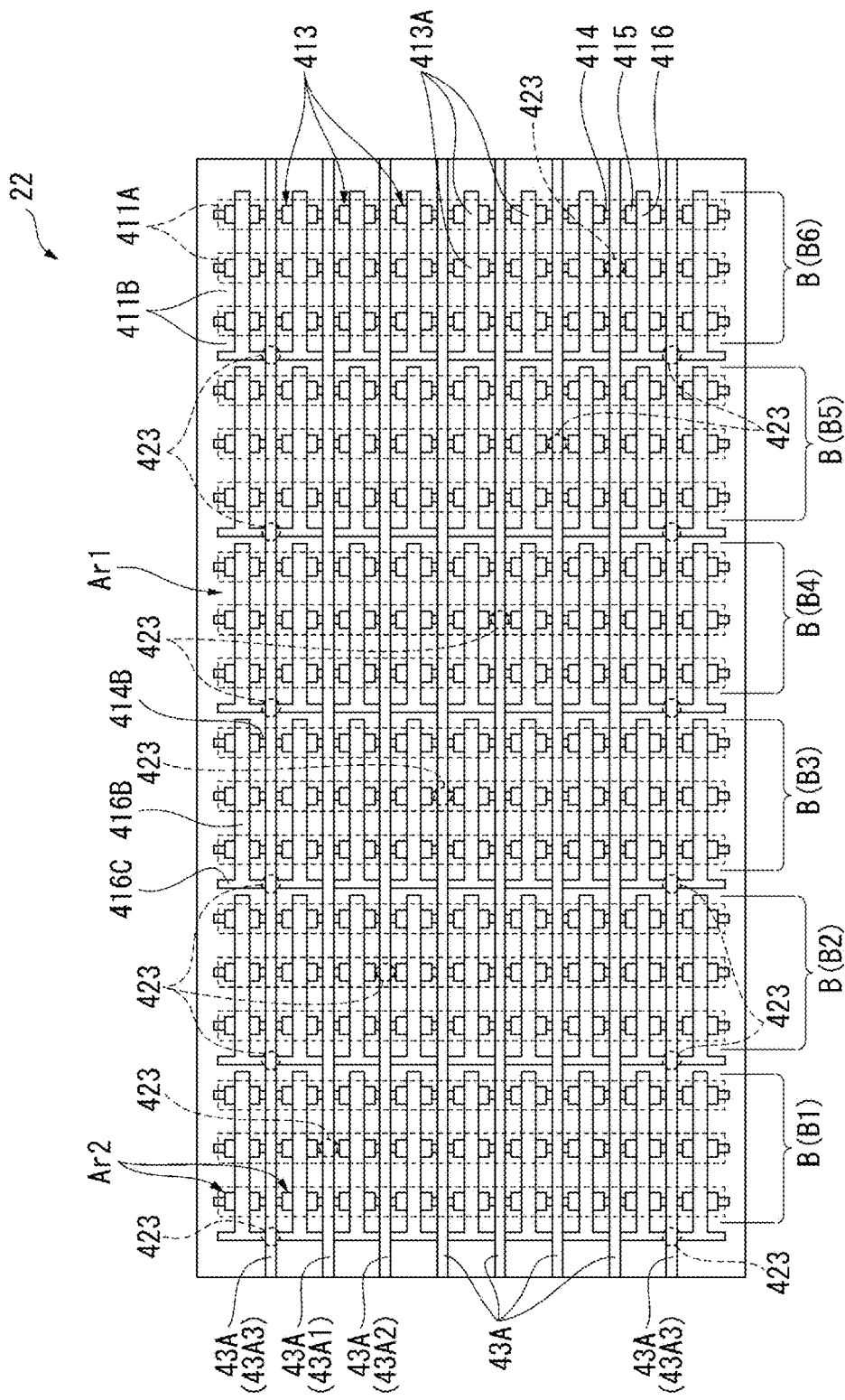
FIG. 9 is a plan view when a base portion in an ultrasonic sensor of a second embodiment is viewed from the sealing plate side.
Figure 10A:
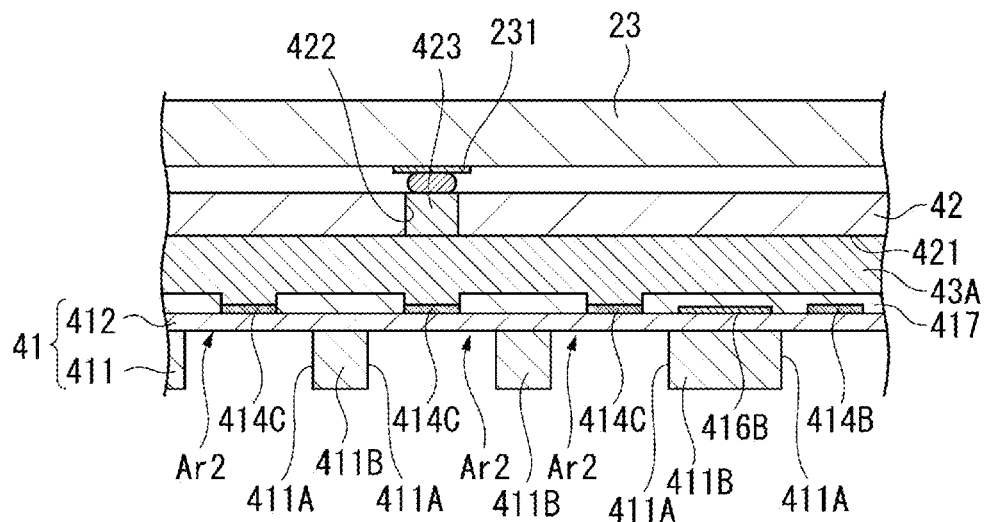
FIGS. 10A and 10B are sectional views schematically showing the ultrasonic sensor of the second embodiment.
Figure 10B:
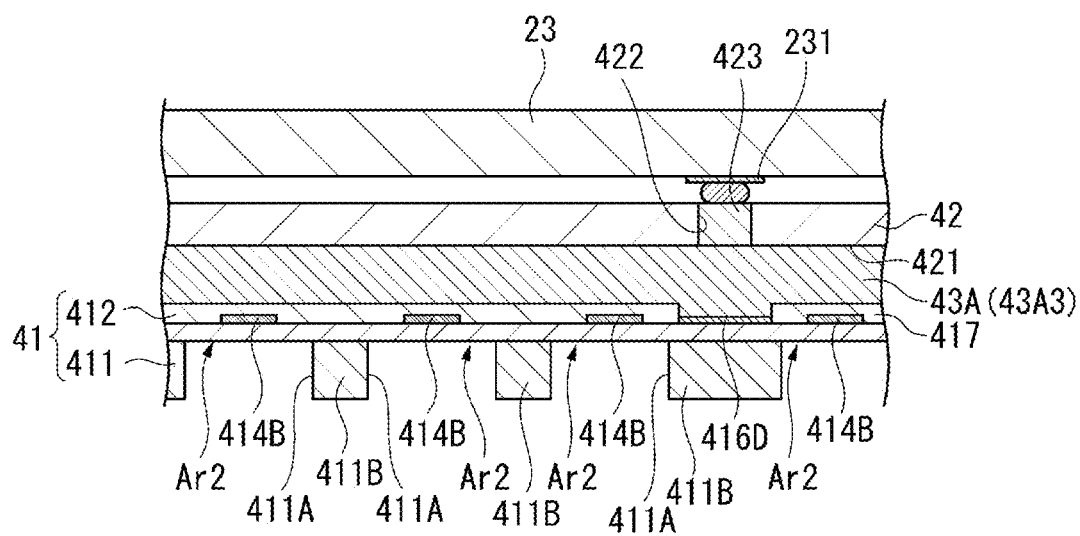

FIG. 9 is a plan view showing the schematic configuration of a base portion of the ultrasonic sensor 22 of the present embodiment. FIG. 10A is a schematic sectional view of the ultrasonic sensor 22 along the longitudinal direction of a suppressing portion 43A electrically connected to the lower electrode 414, and FIG. 10B is a schematic sectional view of the ultrasonic sensor 22 along the longitudinal direction of the suppressing portion 43A electrically connected to the upper electrode 416. In the following explanation, components described previously are denoted by the same reference numerals, and the explanation thereof will be omitted or simplified.

As shown in FIG. 9, in the ultrasonic sensor 22 of the present embodiment, the active portions 413A of a plurality of piezoelectric elements 413 are arranged in a matrix in the array region Ar1, and the piezoelectric elements 413 arranged in the Y direction are connected to each other by the lower electrode 414 continuous along the Y direction, in the same manner as in the first embodiment. The piezoelectric elements 413 arranged in the X direction are connected to each other by the upper electrode 416 continuous along the X direction. In the present embodiment, as shown in FIG. 9, the lower electrodes 414 are not connected to each other at their end positions. Accordingly, the lower electrode terminal 414P is not provided. Similarly, since the upper electrodes 416 are not connected to each other at their end positions, the upper electrode terminal 416P is not provided.

In the present embodiment, the suppressing portion 43A is formed so as to extend in the X direction at the same position as in the first embodiment, that is, between the active portions 413A of the adjacent piezoelectric elements 413, thereby bonding the vibration film 412 and the sealing plate 42 to each other. The suppressing portion 43A of the present embodiment is formed of a resin material containing a conductive filler mixed thereinto, and has conductivity.

In the present embodiment, the insulating layer 417 is not formed on a part of the lower electrode 414 (lower connection wiring line 414B) or a part of the upper electrode 416 (common wiring line 416C).

That is, the suppressing portion 43A for electrically connecting the lower electrode 414 to the circuit board 23 is provided corresponding to each block B. Accordingly, since a part of the lower electrode 414 is in contact with the suppressing portion 43A, the lower electrode 414 is electrically connected to the circuit board 23. In addition, the suppressing portion 43A for electrically connecting the upper electrode 416 to the circuit board 23 is provided. Accordingly, since a part of the upper electrode 416 is in contact with the suppressing portion 43A, the upper electrode 416 is electrically connected to the circuit board 23.

For example, the lower electrode 414 (lower connection wiring line 414B) of the piezoelectric element 413 included in a first block B1 (refer to FIG. 9) disposed in the array region Ar1 forms a lower electrode conducting portion 414C (refer to FIG. 10A), on which the insulating layer 417 is not formed, in a portion where a first suppressing portion 43A1 is laminated. Then, the first suppressing portion 43A1 is formed on the lower electrode conducting portion 414C of the lower electrode 414. Accordingly, the first suppressing portion 43A1 and the lower electrode 414 of the first block B1 come into contact with each other to be electrically connected to each other.

The lower electrode 414 (lower connection wiring line 414B) of the piezoelectric element 413 included in a second block B2 at a different position from the first block B1 forms a lower electrode conducting portion 414C, on which the insulating layer 417 is not formed, in a portion where a second suppressing portion 43A2 is laminated. Then, the second suppressing portion 43A2 is formed on the lower electrode conducting portion 414C of the lower electrode 414. Accordingly, the second suppressing portion 43A2 and the lower electrode 414 of the second block B2 come into contact with each other to be electrically connected to each other.

The same is true for the other blocks B, and the suppressing portion 43A that is electrically connected corresponding to each block is present.

In the present embodiment, as in the first embodiment, the upper electrodes 416 of the respective piezoelectric elements 413 arranged in the array region Ar1 are connected to each other by the upper connection wiring line 416B and the common wiring line 416C. Then, as shown in FIG. 10B, the common wiring line 416C forms an upper electrode conducting portion 416D, on which the insulating layer 417 is not formed, in a portion where a third suppressing portion 43A3 corresponding to the upper electrode 416 is laminated. Then, the third suppressing portion 43A3 is formed on the upper electrode conducting portion 416D. Accordingly, each upper electrode 416 and the third suppressing portion 43A3 come into contact with each other to be electrically connected to each other.

On the other hand, as shown in FIGS. 10A and 10B, the sealing plate 42 has at least one through hole 422, which passes through the sealing plate 42 in the film thickness direction, at a position facing each suppressing portion 43A. A penetrating electrode 423 is inserted through the through hole 422, so that the suppressing portion 43A is brought into contact with (bonded to) one end of the penetrating electrode 423. The other end of the penetrating electrode 423 is connected to the substrate terminal portion 231 provided on the circuit board 23 by, for example, a conductive member, such as solder.

In the suppressing portion 43A (for example, the suppressing portion 43A1 or the suppressing portion 43A2 shown in FIG. 9) electrically connected to the lower electrode 414, a position where the through hole 422 and the penetrating electrode 423 are provided is preferably a position where the lower electrode conducting portion 414C is provided. In the present embodiment, the block B of 1 ch is formed by three groups of piezoelectric elements, and three lower electrode conducting portions 414C arranged in the X direction with respect to one suppressing portion 43B are provided. In this case, as shown in FIGS. 9 and 10A, it is preferable to provide the penetrating electrode 423 at a position facing the lower electrode conducting portion 414C at the center (position overlapping the lower electrode conducting portion 414C at the center in a plan view). In addition, the three penetrating electrodes 423 may be provided so as to face the three lower electrode conducting portions 414C.

The same is true for the suppressing portion 43A (43A3) electrically connected to the upper electrode 416, a position where the through hole 422 and the penetrating electrode 423 are provided is preferably a position where the upper electrode conducting portion 416D is provided. For example, in the present embodiment, as shown in FIG. 9, the penetrating electrode 423 is provided at a position facing the upper electrode conducting portion 416D (position overlapping the upper electrode conducting portion 416D in a plan view) of the common wiring line 416C at the center of the array region Art. In addition, a plurality of penetrating electrodes 423 may be provided so as to face the respective upper electrode conducting portions 416D.

Effect of the Present Embodiment

In the ultrasonic sensor 22 of the present embodiment, the suppressing portion 43A is formed of a resin material containing a conductive filler. The suppressing portion 43A is provided longitudinally along the X direction between the adjacent active portions 413A, and is connected to the lower electrode conducting portion 414C of the lower electrode 414 connected to each active portion 413A or the upper electrode conducting portion 416D of the upper electrode 416.

In such a configuration, for example, as in the first embodiment, the lower electrode 414 or the upper electrode 416 does not need to be drawn out to the lower electrode terminal 414P or the upper electrode terminal 416P of the outer peripheral portion of the substrate 411. For this reason, the lower electrode 414 or the upper electrode 416 can be electrically connected to the circuit board 23 through the suppressing portion 43A. Therefore, it is possible to simplify the wiring configuration. In addition, since a signal can be input to a position near the active portion 413A when inputting a signal to each active portion 413A, it is possible to suppress the influence of a voltage drop. As a result, it is possible to improve the efficiency of ultrasonic wave transmission and reception of the ultrasonic sensor 22.

In the present embodiment, the sealing plate 42 includes the penetrating electrode 423 that penetrates in the plate thickness direction, and the suppressing portion 43A is electrically connected by being bonded onto the penetrating electrode 423. That is, the suppressing portion 43A is connected to a wiring portion that is a surface of the penetrating electrode 423 facing the vibration film 412. In such a configuration, it is not necessary to separately connect a lead wire, an FPC, or the like to the suppressing portion 43A, and the lower electrode 414 or the upper electrode 416 and the penetrating electrode 423 can be electrically connected to each other through the suppressing portion 43A just by bonding the suppressing portion 43A to the sealing plate 42.

In the present embodiment, the other end portion of the penetrating electrode 423 not facing the vibration film 412 is electrically connected to a terminal portion of the circuit board 23 that is disposed on a side of the sealing plate 42 not facing the base portion 41. Thus, each piezoelectric element 413 can be easily electrically connected to the circuit board 23 without using an FPC or the like.

Modification Examples

The invention is not limited to the embodiments described above, but various modifications, improvements, and appropriate combinations of the respective embodiments may be made in a range where the object of the invention can be achieved.

In the first embodiment described above, an example is shown in which the block B of one channel is formed by three groups of piezoelectric elements. However, the invention is not limited thereto. For example, the block B of one channel may be formed by one group of piezoelectric elements, or the block B of one channel may be formed by two or four or more groups of piezoelectric elements. The lower electrode 414 of each piezoelectric element 413 may have an independent terminal portion, so that each piezoelectric element 413 is independently driven. In addition, although the configuration has been exemplified in which a plurality of blocks B are arranged along the X direction, it is possible to adopt a configuration in which a plurality of blocks B are arranged along the Y direction, a configuration in which a plurality of blocks B are arranged in a matrix along the X and Y directions, and the like.

In the embodiment described above, the opening 411A and the piezoelectric element 413 are formed so that all active portions 413A arranged along the Y direction are included in a position overlapping one opening 411A in a plan view. However, the invention is not limited thereto.

For example, "n" openings 411A longitudinal in the Y direction may be arranged along the Y direction, and "m" active portions 413A may be arranged side by side along the Y direction in a region overlapping each opening 411A. In this case, "n×m" piezoelectric elements 413 arranged in the Y direction are connected to each other by the lower electrode 414, thereby forming a group of piezoelectric elements.

In the embodiment described above, it is assumed that the active portion 413A and the opening 411A are rectangles (including squares) in a plan view. However, the shape of the active portion 413A may not be a rectangle. The shape of the active portion 413A may not be a perfect rectangle. For example, a shape that generally looks rectangular even though the corner is round or the side is somewhat uneven may be applied, or a quadrangle other than the rectangle, a polygon, a circle, or an ellipse may be applied.

In the embodiment described above, the suppressing portions 43 and 43A are provided only in a portion where the partition wall 411B is not present between the adjacent vibration regions Ar2 (active portions 413A), and are not provided in a portion where the partition wall 411B is present. However, the suppressing portions 43 and 43A may be provided in a portion where the partition wall 411B is located. For example, the suppressing portions 43 and 43A may be provided along edge portions (sides of ±Y side end portions) of the opening 411A along the X direction or edge portions (sides of ±X side end portions) of the opening 411A along the Y direction.

In the embodiment described above, an example is shown in which the opening 411A is longitudinal in the Y direction and a plurality of active portions 413A arranged in the Y direction are arranged in the opening 411A. However, the active portions 413A arranged in a matrix along the X and Y directions may be provided in the opening 411A. In this case, the suppressing portion 43 is also disposed between the active portions 413A adjacent to each other along the X direction. Therefore, it is possible to form the vibration region Ar2 corresponding to each active portion 413A.

In the second embodiment, an example is shown in which the penetrating electrode 423 is provided on the sealing plate 42. However, for example, a wiring portion in contact with the suppressing portion 43A (wiring portion not penetrating the sealing plate 42) may be provided on the substrate surface of the sealing plate 42. In this case, a circuit pattern connected to a wiring terminal portion may be formed on the surface of the sealing plate 42A, and a part of the circuit pattern may be connected to the circuit board 23.

In each of the embodiments described above, the suppressing portions 43 and 43A that are continuous across both end portions of the base portion 41 along the X direction has been exemplified. However, the invention is not limited thereto.

Figure 11:
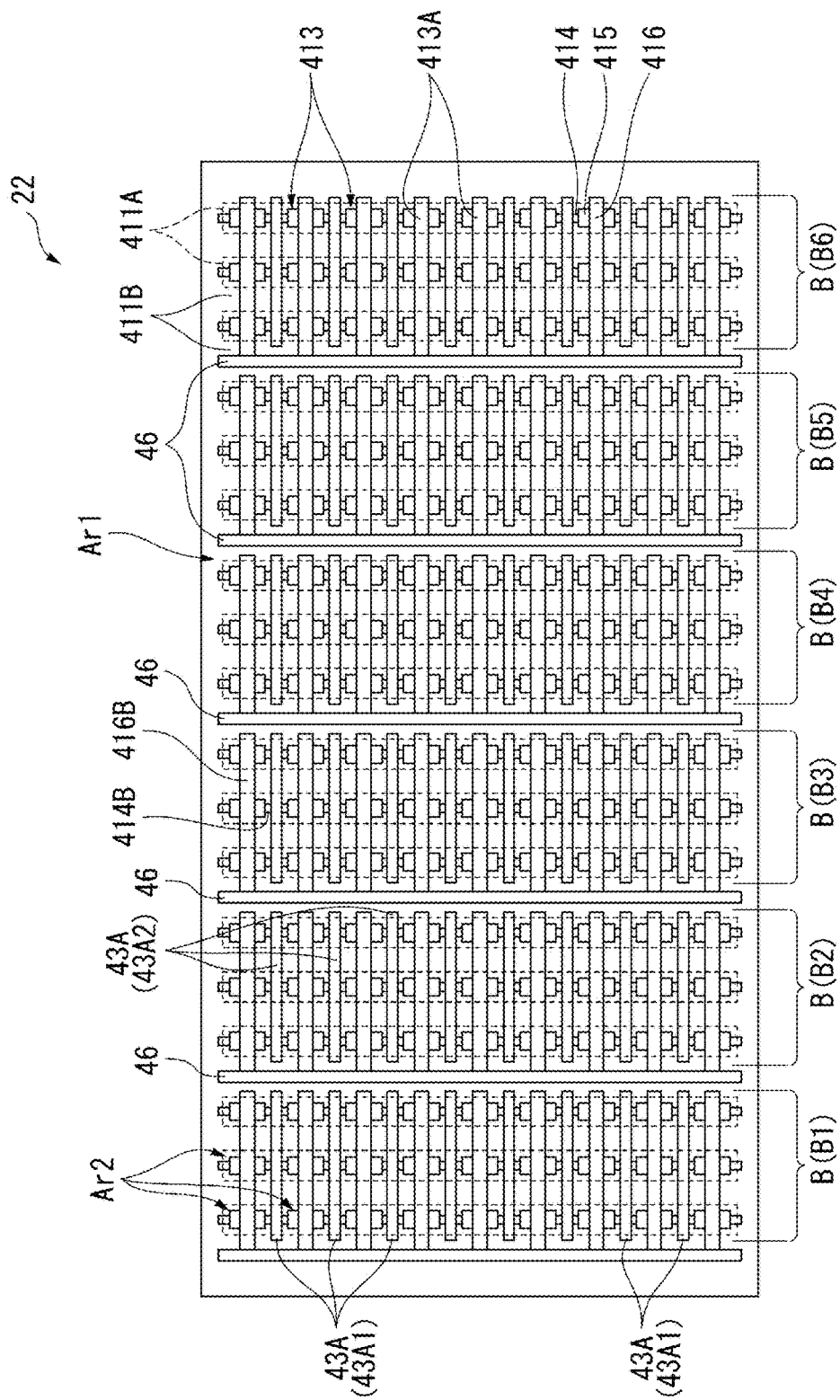
FIG. 11 is a plan view when a base portion in an ultrasonic sensor in a modification example is viewed from the sealing plate side.

FIG. 11 is a diagram showing the schematic configuration of a substrate in a modification example.

For example, as shown in FIG. 11, the suppressing portion 43A (or the suppressing portion 43) may be provided between both end portions of one block B in the X direction in a plan view. In FIG. 11, an example is shown in which the suppressing portion 43 is provided in units of the block B. However, the suppressing portion 43A (or the suppressing portion 43) may be provided in units of the opening 411A.

In these configurations, between the adjacent blocks B, a bonding portion 46 that is longitudinal along the Y direction may be provided on the common wiring line 416C. Since the bonding portion 46 can be formed of, for example, the same resin material as the suppressing portion 43A (or the suppressing portion 43), the bonding portion 46 can be formed simultaneously with the suppressing portion 43. In this case, since the sealing plate 42 and the base portion 41 can be bonded to each other along the X direction by the suppressing portion 43A and the sealing plate 42 and the base portion 41 can be bonded to each other along the Y direction by the bonding portion 46, it is possible to further increase the bonding strength.

In the second embodiment, a configuration may be applied in which the suppressing portion 43A or the bonding portion 46 is formed as shown in FIG. 11. In this case, each lower connection wiring line 414B that connects the active portions 413A to each other can be used as the lower electrode conducting portion 414C. For example, as shown in FIG. 11, all the suppressing portions 43A present in the first block B1 become the first suppressing portions 43A1 electrically connected to the lower electrode 414 of the first block B1. In addition, all the suppressing portions 43A present in the second block B2 become the second suppressing portions 43A2 electrically connected to the lower electrode 414 of the second block B2. In this case, since a signal can be input and output at a position closer to each active portion 413A, it is possible to further suppress the influence of a voltage drop.

For the upper electrode 416, the bonding portion 46 may be formed of a resin material containing a conductive filler, and the upper electrode conducting portion 416D may be provided at each intersection position between the upper connection wiring line 416B and the common wiring line 416C. In a case where the bonding portion 46 is formed over all the upper electrodes 416 arranged in the Y direction, the common wiring line 416C does not need to be formed, and the upper electrodes 416 are connected to each other by the bonding portion 46 having conductivity.

In the embodiment described above, the piezoelectric element 413 in which the lower electrode 414, the piezoelectric layer 415, and the upper electrode 416 are laminated in the thickness direction of the vibration film 412 has been exemplified as a vibration element. However, the invention is not limited thereto. For example, on the one surface side of the piezoelectric layer perpendicular to the thickness direction, a pair of electrodes may be disposed so as to face each other. Alternatively, on the side surface of the piezoelectric layer along the thickness direction, electrodes may be disposed so as to interpose a piezoelectric layer therebetween.

Instead of using the piezoelectric layer, a vibration element may be used that includes a first electrode provided on the vibration film 412 and a second electrode (for example, disposed on the sealing plate 42) facing the first electrode with an air gap interposed therebetween and that vibrates the vibration film 412 with electrostatic force or detects the vibration of the vibration film 412.

In each of the embodiments described above, the ultrasonic sensor 22 (ultrasonic transducer) provided in the ultrasonic probe 2 of the ultrasonic measurement apparatus 1 that is an ultrasonic apparatus has been exemplified. However, the invention is not limited thereto. The invention can also be applied to any vibration device for vibrating a predetermined vibration region of a vibration film. For example, when vibrating a desired vibration region of a vibration plate (vibration film) used in a microphone, a speaker, or the like, a desired vibration region may be formed by supporting a surface on one side in the thickness direction of the vibration film with a partition wall of an opening of a substrate and bonding the other surface to a sealing plate through a suppressing portion.

As the ultrasonic measurement apparatus 1, a configuration for measuring the internal tomographic structure of the living body has been exemplified. However, the ultrasonic measurement apparatus 1 can also be used as a measurement apparatus for examining the internal structure of concrete, such as a concrete building, for example.

In addition, although the ultrasonic measurement apparatus 1 including the ultrasonic sensor 22 has been exemplified. However, the invention can also be applied to other ultrasonic apparatuses. For example, the invention can also be used for an ultrasonic washing machine including an ultrasonic transducer that washes an object to be cleaned by sending ultrasonic waves to the object to be cleaned.

In addition, specific structures when implementing the invention may be formed by appropriately combining the embodiments and the modification examples described above in a range where the object of the invention can be achieved, or may be appropriately changed to other structures in a range where the object of the invention can be achieved.

The entire disclosure of Japanese Patent Application No. 2016-020036, filed on Feb. 4, 2016 is expressly incorporated by reference herein.

What is claimed is:
1. An ultrasonic transducer, comprising:
   a substrate in which an opening is formed;
   a vibration film that is provided on the substrate so as to close the opening;
   a plurality of vibration elements that perform at least one of driving processing for driving the vibration film to vibrate and detection processing for detecting vibration of the vibration film and that are disposed at positions where the vibration film and the opening overlap each other in a plan view along a thickness direction of the vibration film;
   a support substrate that is disposed so as to face the vibration film, supports the vibration film, and has a surface facing the vibration film as a flat surface; and
   a suppressing portion that is provided between the adjacent vibration elements in the plan view, is bonded to, and sandwiched between, both the vibration film and the support substrate, and is formed of a resin material for suppressing transmission of vibration of the vibration film.

2. The ultrasonic transducer according to claim 1,
   wherein a connection wiring line connected to the vibration element is provided on the vibration film, and
   the suppressing portion contains a conductive filler, and is connected to the connection wiring line.

3. The ultrasonic transducer according to claim 2,
wherein the support substrate has a wiring portion, which is connected to the suppressing portion, on a surface facing the vibration film.

4. The ultrasonic transducer according to claim 3,
wherein the support substrate includes a penetrating electrode that penetrates the support substrate in a thickness direction to connect the wiring portion and a circuit board, on which a circuit for controlling the vibration element is provided, to each other.

5. An ultrasonic probe, comprising:
an ultrasonic transducer; and
a housing in which the ultrasonic transducer is housed,
wherein the ultrasonic transducer includes:
  a substrate in which an opening is formed;
  a vibration film that is provided on the substrate so as to close the opening;
  a plurality of vibration elements that perform at least one of driving processing for driving the vibration film to vibrate and detection processing for detecting vibration of the vibration film and that are disposed at positions where the vibration film and the opening overlap each other in a plan view along a thickness direction of the vibration film;
  a support substrate that is disposed so as to face the vibration film, supports the vibration film, and has a surface facing the vibration film as a flat surface; and
  a suppressing portion that is provided between the adjacent vibration elements in the plan view, is bonded to, and sandwiched between, both the vibration film and the support substrate, and is formed of a resin material for suppressing transmission of vibration of the vibration film.

6. An ultrasonic apparatus, comprising:
an ultrasonic transducer; and
a control unit that controls the ultrasonic transducer,
wherein the ultrasonic transducer includes:
a substrate in which an opening is formed;
a vibration film that is provided on the substrate so as to close the opening;
a plurality of vibration elements that perform at least one of driving processing for driving the vibration film to vibrate and detection processing for detecting vibration of the vibration film and that are disposed at positions where the vibration film and the opening overlap each other in a plan view along a thickness direction of the vibration film;
a support substrate that is disposed so as to face the vibration film, supports the vibration film, and has a surface facing the vibration film as a flat surface; and
a suppressing portion that is provided between the adjacent vibration elements in the plan view, is bonded to, and sandwiched between, both the vibration film and the support substrate, and is formed of a resin material for suppressing transmission of vibration of the vibration film.

7. An ultrasonic transducer manufacturing method, comprising:
forming, on a vibration film of a substrate in which the vibration film is provided, a plurality of vibration elements for performing at least one of driving processing for driving the vibration film to vibrate and detection processing for detecting vibration of the vibration film;
forming a suppressing portion, which is formed of a resin material for suppressing transmission of vibration of the vibration film, on a surface of the vibration film not facing the substrate and between the adjacent vibration elements in a plan view along a thickness direction of the vibration film;
making a support substrate, which has a surface facing the vibration film as a flat surface, face the surface of the vibration film not facing the substrate and bonding the other end portion of the suppressing portion, which is on an opposite side to one end portion of the suppressing portion connected to the vibration film, to the support substrate by heating; and
forming an opening in the substrate such that the plurality of vibration elements are disposed at positions where the vibration film and the opening overlap each other in the plan view,
wherein the suppressing portion is bonded to, and sandwiched between, both the vibration film and the support substrate.

8. A vibration device, comprising:
a vibration film that has a predetermined thickness and is able to vibrate in a thickness direction;
a support substrate that is disposed so as to face the vibration film, supports the vibration film, and has a surface facing the vibration film as a flat surface; and
a suppressing portion that is provided along a vibration region in the vibration film and suppresses transmission of vibration of the vibration region of the vibration film to a region other than the vibration region,
wherein the suppressing portion is formed of a resin material, and is bonded to, and sandwiched between, both the vibration film and the support substrate.

* * * * *